(12) United States Patent
Keating

(10) Patent No.: US 9,663,411 B2
(45) Date of Patent: May 30, 2017

(54) FERMENTED SOIL ADDITIVE

(71) Applicant: LIQUID FERTILISER SYSTEMS PTY LTD, Forrestdale (AU)

(72) Inventor: Peter James Keating, Forrestdale (AU)

(73) Assignee: LIQUID FERTILISER SYSTEMS PTY LTD, Forrestdale, Western Australia (AU)

( * ) Notice: Subject to any disclaimer, the term of this patent is extended or adjusted under 35 U.S.C. 154(b) by 0 days.

(21) Appl. No.: 14/648,013

(22) PCT Filed: Nov. 29, 2013

(86) PCT No.: PCT/AU2013/001383
§ 371 (c)(1),
(2) Date: May 28, 2015

(87) PCT Pub. No.: WO2014/082130
PCT Pub. Date: Jun. 5, 2014

(65) Prior Publication Data
US 2016/0068450 A1 Mar. 10, 2016

(30) Foreign Application Priority Data

Nov. 29, 2012 (AU) ................ 2012905205
Apr. 16, 2013 (AU) ................ 2013901319

(51) Int. Cl.
*C05F 5/00* (2006.01)
*A01N 63/02* (2006.01)
*C09K 17/42* (2006.01)

(52) U.S. Cl.
CPC ............. *C05F 5/00* (2013.01); *A01N 63/02* (2013.01); *C05F 5/008* (2013.01); *C09K 17/42* (2013.01); *Y02W 30/47* (2015.05)

(58) Field of Classification Search
CPC . C05F 5/00; C05F 5/008; A01N 63/02; C09K 17/42; Y02W 30/47
See application file for complete search history.

(56) References Cited

U.S. PATENT DOCUMENTS

| | | | |
|---|---|---|---|
| 3,561,944 A | 2/1971 | Batttistoni et al. | |
| 3,635,797 A * | 1/1972 | Battistoni | C02F 3/342 210/606 |
| 3,943,078 A | 3/1976 | James | |
| 4,336,051 A | 6/1982 | Marquez | |
| 2010/0272701 A1 | 10/2010 | Chen | |
| 2013/0266532 A1 | 10/2013 | Kim | |

FOREIGN PATENT DOCUMENTS

| | | |
|---|---|---|
| CA | 888164 A | 12/1971 |
| CN | 1171384 A | 1/1998 |
| CN | 1546437 A | 11/2004 |
| CN | 101157860 A | 4/2008 |
| CN | 101250066 A | 8/2008 |
| CN | 101816280 A | 9/2010 |
| CN | 101913963 A | 12/2010 |
| DE | 3840059 A1 | 5/1990 |
| HU | 30671 T | 3/1984 |
| JP | 47029155 A | 4/1972 |
| JP | 62012688 A | 1/1987 |
| JP | H-04164009 A | 6/1992 |
| JP | 7274942 A | 10/1995 |
| JP | 3139273 B2 | 2/2001 |
| JP | 2003095773 A | 4/2003 |
| KR | 2010021154 A | 2/2010 |
| KR | 2010024619 A | 3/2010 |
| KR | 20120092290 A | 8/2012 |
| WO | WO-02/102740 A1 | 12/2002 |
| WO | WO-2004/020367 A1 | 3/2004 |
| WO | WO-2009/083819 A1 | 7/2009 |
| WO | WO-2010/025518 A1 | 3/2010 |
| WO | WO-2012/005495 A2 | 1/2012 |

OTHER PUBLICATIONS

E. Denise Baxter & Paul S. Hughes, Beer: Quality, Safety and Nutritional Aspects 98-119 ( Royal Society of Chemistry 2001).*
Brackman et al., Structure-activity relationship of cinnamaldehyde analogs as inhibitors of Al-2 based quorum sensing and their effect on virulence of vibrio spp. *PLoS ONE* 6(1): e16084 (2011).
Carter et al., Pathway engineering via quorum sensing and sRNA riboregulators-interconnected networks and controllers. *Metab. Eng.* 14; 281-8 (2012).
Cirou et al., Efficient biostimulation of native and introduced quorum-quenching *Rhodococcus erythropolis* populations is revealed by a combination of analytical chemistry, microbiology, and pyrosequencing. *Appl. Environ. Microbiol.* 78(2); 481-92 (2012).
Jolivet, B (PhD Thesis), Synthesis of some furanone derivatives: Putative quorum sensing or chitinase inhibitors (2005).
Lahrmann et al., Host-related metabolic cues affect colonization strategies of a root endophyte. *Proc. Natl. Acad. Sci. USA* 110(34): 13965-70 (2013).
International Search Report and Written Opinion of the International Searching Authority issued in connection with International Application No. PCT/AU2013/001383, dated Jan. 29, 2014.

* cited by examiner

*Primary Examiner* — Sean Basquill
(74) *Attorney, Agent, or Firm* — Marshall, Gerstein & Borun LLP

(57) ABSTRACT

A soil additive comprising a sugar ferment wherein said ferment contains signalling molecules comprising between about 1-50% of the organic matter present in the ferment.

22 Claims, 25 Drawing Sheets

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Soil Bacterial Community I

<400> SEQUENCE: 1
gtcgtaacaa ggtagccgta                                              20

<210> SEQ ID NO 2
<211> LENGTH: 15
<212> TYPE: DNA
<213> ORGANISM: Artificial Sequence
<220> FEATURE:
<223> OTHER INFORMATION: Soil Bacterial Community I

<400> SEQUENCE: 2
gccaaggcat ccacc                                                   15

<210> SEQ ID NO 3
<211> LENGTH: 20
<212> TYPE: DNA
<213> ORGANISM: Artificial Sequence
<220> FEATURE:
<223> OTHER INFORMATION: Soil Bacterial Community II

<400> SEQUENCE: 3
tgcggctgga tccctcctt                                               20

<210> SEQ ID NO 4
<211> LENGTH: 18
<212> TYPE: DNA
<213> ORGANISM: Artificial Sequence
<220> FEATURE:
<223> OTHER INFORMATION: Soil Bacterial Community II

<400> SEQUENCE: 4
ccgggtttcc ccattcgg                                                18

<210> SEQ ID NO 5
<211> LENGTH: 16
<212> TYPE: DNA
<213> ORGANISM: Artificial Sequence
<220> FEATURE:
<223> OTHER INFORMATION: Soil Bacterial Community III

<400> SEQUENCE: 5
tgyacacacc gcccgt                                                  16

<210> SEQ ID NO 6
<211> LENGTH: 16
<212> TYPE: DNA
<213> ORGANISM: Artificial Sequence
<220> FEATURE:
<223> OTHER INFORMATION: Soil Bacterial Community III

<400> SEQUENCE: 6
gggttbcccc attcrg                                                  16

<210> SEQ ID NO 7
<211> LENGTH: 18
<212> TYPE: DNA
<213> ORGANISM: Unknown

```
<220> FEATURE:
<223> OTHER INFORMATION: Archaea

<400> SEQUENCE: 7
ccgacggtga grgrygaa                                                   18

<210> SEQ ID NO 8
<211> LENGTH: 17
<212> TYPE: DNA
<213> ORGANISM: Unknown
<220> FEATURE:
<223> OTHER INFORMATION: Archaea

<400> SEQUENCE: 8
acgggcggtg wgtrcaa                                                    17

<210> SEQ ID NO 9
<211> LENGTH: 15
<212> TYPE: DNA
<213> ORGANISM: Unknown
<220> FEATURE:
<223> OTHER INFORMATION: Actinobacteria

<400> SEQUENCE: 9
taccggaagg tgcgg                                                      15

<210> SEQ ID NO 10
<211> LENGTH: 22
<212> TYPE: DNA
<213> ORGANISM: Unknown
<220> FEATURE:
<223> OTHER INFORMATION: Actinobacteria

<400> SEQUENCE: 10
gggtactgag atgtttcact tc                                              22

<210> SEQ ID NO 11
<211> LENGTH: 22
<212> TYPE: DNA
<213> ORGANISM: Unknown
<220> FEATURE:
<223> OTHER INFORMATION: Dikarya fungi

<400> SEQUENCE: 11
cttggtcatt tagaggaagt aa                                              22

<210> SEQ ID NO 12
<211> LENGTH: 20
<212> TYPE: DNA
<213> ORGANISM: Unknown
<220> FEATURE:
<223> OTHER INFORMATION: Dikarya fungi

<400> SEQUENCE: 12
tcctccgctt attgatatgc                                                 20

<210> SEQ ID NO 13
<211> LENGTH: 17
<212> TYPE: DNA
<213> ORGANISM: Unknown
<220> FEATURE:
<223> OTHER INFORMATION: Firmicutes

<400> SEQUENCE: 13
gacaggtggt gcatggt                                                    17
```

```
<210> SEQ ID NO 14
<211> LENGTH: 16
<212> TYPE: DNA
<213> ORGANISM: Unknown
<220> FEATURE:
<223> OTHER INFORMATION: Actinobacteria

<400> SEQUENCE: 14
tacggccgca aggcta                                                16

<210> SEQ ID NO 15
<211> LENGTH: 16
<212> TYPE: DNA
<213> ORGANISM: Unknown
<220> FEATURE:
<223> OTHER INFORMATION: Gram Positive Proteobacteria

<400> SEQUENCE: 15
catcatggcc cttacg                                                16

<210> SEQ ID NO 16
<211> LENGTH: 18
<212> TYPE: DNA
<213> ORGANISM: Unknown
<220> FEATURE:
<223> OTHER INFORMATION: Archaea

<400> SEQUENCE: 16
ccgacggtga grgrygaa                                              18

<210> SEQ ID NO 17
<211> LENGTH: 21
<212> TYPE: DNA
<213> ORGANISM: Unknown
<220> FEATURE:
<223> OTHER INFORMATION: Acidobacteria

<400> SEQUENCE: 17
gaaccttacc tgggctcgaa a                                          21

<210> SEQ ID NO 18
<211> LENGTH: 19
<212> TYPE: DNA
<213> ORGANISM: Unknown
<220> FEATURE:
<223> OTHER INFORMATION: Bacteriodetes

<400> SEQUENCE: 18
atacgcgagg aaccttacc                                             19
```

FERMENTED SOIL ADDITIVE

TECHNICAL FIELD

The present invention relates to a fermented sugar based soil additive for improving soil and methods for producing the same.

BACKGROUND ART

The following discussion of the background art is intended to facilitate an understanding of the present invention only. The discussion is not an acknowledgement or admission that any of the material referred to is or was part of the common general knowledge as at the priority date of the application.

Increased soil organic matter content confers productivity benefits to agricultural soil. Such benefits include improving soil structure by increasing aggregate stability, improving water holding capacity, improving soil nutrient content and availability to plants and conferring resistance to root disease. Methods to increase soil carbon can provide commercial benefits to crop and grain producers by producing higher yields for lower input costs and by sequestering carbon in soil.

Soil organic matter originates with carbon dioxide from the atmosphere becoming transformed by plant photosynthesis into plant biomass. Such plant biomass becomes an energy source for soil microbes which break down the organic matter by oxidation, leaving residues which are refractory to further decomposition and thus accumulate in soil. The progressive accumulation of refractory and stable organic matter increases the amount of soil carbon in a form which improves both the structure and the fertility of soils.

Studies of the biochemical mechanisms involved in the oxidative breakdown of plant residues have shown that woody residues containing substances such as suberin and lignin are not easily oxidised. Organisms capable of breaking down such refractory substances require high energy catalytic reactions to enable ring-cleavage, wherein the energy available in phenolic residues becomes available for metabolism. Such organisms typically belong to higher orders of soil microbes, including the higher fungi Dikarya, and higher bacteria Actinobacteria. These microbes have more sophisticated growth requirements than the lower orders of soil microbes such as the simple bacteria Proteobacteria and Firmicutes. Whilst the lower orders of microbes can grow on simple substrates such as sugar, higher orders of microbes require growth factors which include vitamins and higher molecular weight organic substrates. In a natural soil, the growth factors required by higher microbes are typically provided by the biomass and detritus produced by the lower microbial orders.

Soil priming is a phenomenon wherein when organic matter is added to soil it stimulates microbial respiration, often to the point where the total amount of organic matter oxidised exceeds the amount added. In the earliest days, the organic additions were things like leaf litter, straw or manure. In the last five or so years, researchers have added progressively smaller amount of purer substances like glucose and amino acids. It transpires that the initial burst of activity comes from the simple bacteria like Proteobacteria, which ecologically are k-strategists—meaning they grow rapidly feeding off simple media so can dominate the overall microbial population. This activity abates over time, and R-strategists take over. R-strategists are microbes with more sophisticated growth requirements, generally oligotrophs which can survive with lower energy availability and generally have much higher biodiversity than k-strategists.

Techniques such as metagenomics (the study of genetic material recovered directly from environmental samples) have been developed to study soil microbial ecology. Metagenomics typically uses shot-gun sequencing or pyrosequencing to determine the nature of DNA extracted from microbes in soil, allowing the production of a profile of microbial diversity in a natural sample. When soil microbes are grouped according to their phylogeny, metagenomics shows that many taxa are present within each of the major groups, and the proportionality of the groups and the taxa within those groups changes according to the physical, chemical and environmental attributes of the soil.

Metagenomics has shown that the cultivation of soils for agricultural production, and the application of fertilisers and other agricultural chemicals, causes profound alteration to the microbial populations in soil. Agricultural use generally causes a relative increase in the number of individuals and taxa in the lower orders of soil microbes and a decrease in the numbers and taxa of higher orders of soil microbes. Furthermore, the clearing of natural vegetation and the use of land for agriculture causes a substantial decline in soil organic matter. As it is soil organic matter which provides the growth substrate for soil microbes, the clearing of land for agriculture can cause a significant loss of microbial diversity.

It is against this background that the present invention has been developed.

The present invention seeks to provide the consumer with a useful or commercial choice of soil additive for the improvement of soil structure and/or fertility through the enhancement of net plant productivity

SUMMARY OF INVENTION

The present invention provides a soil additive comprising a sugar ferment wherein said ferment contains signalling molecules comprising between about 1-50% of the organic matter present in the ferment.

Preferably, the signalling molecules of the soil additive are selected from one or more of the following groups: microbial quorum sensors and quenchers, biocides or plant elicitors The invention further provides a method for producing a soil additive comprising a sugar ferment comprising the step of:
  a) fermenting sugar using a microbe under conditions of high metabolic stress
wherein the conditions of high metabolic stress result in production of high levels of signalling molecules by the microbe.

There is also provided a kit for conditioning soil, comprising:
  a) soil additive comprising a sugar ferment wherein said ferment contains signalling molecules comprising between about 1-50% (w/w) of the organic matter present in the ferment; and
  b) instructions for administration of said soil additive.

There is also provided a method for conditioning soil, comprising the step of:
  a) adding to the soil an amount of soil additive comprising a sugar ferment wherein said ferment contains signalling molecules comprising between about 1-50% (w/w) of the organic matter present in the ferment.

There is further provided a method for promoting plant growth, comprising the step of:
a) adding to the soil an amount of soil additive comprising a sugar ferment wherein said ferment contains signalling molecules comprising between about 1-50% (w/w) of the organic matter present in the ferment.

There is also provided a method for increasing crop yield, comprising the steps of:
a) adding to the soil an amount of soil additive comprising a sugar ferment wherein said ferment contains signalling molecules comprising between about 1-50% (w/w) of the organic matter present in the ferment.

There is also provided a method for modifying the population composition of rhizosphere microflora, comprising the step of:
a) adding to the soil an amount of soil additive comprising a sugar ferment wherein said ferment contains signalling molecules comprising between about 1-50% (w/w) of the organic matter present in the ferment.

BRIEF DESCRIPTION OF THE DRAWINGS

The description will be made with reference to the accompanying drawings in which.

DETAILED DESCRIPTION

Detailed Description of the Invention

Figure 1:
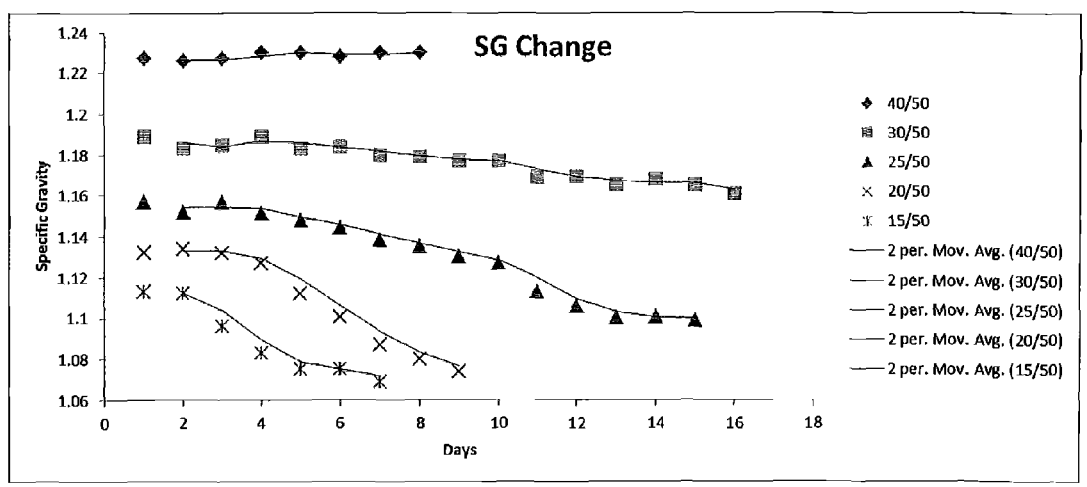
FIG. 1 is a graph of the change in specific gravity during fermentation of a molasses solution according to the present invention over time.

In accordance with the present invention, there is provided a fermented sugar based soil additive for improving soil. The advantage of the present invention lies in the ability to convert sugars from a variety of sources into a mixture of complex organic molecules which have similarities in both structure and composition to the mixture of complex organic molecules used by plants to signal microbial populations, and used within microbial populations for signalling. The complex organic molecules produced from a sugar source act as signalling molecules to modify soil microbiology, resulting in increased plant productivity.

Soil Additive

In one embodiment, the present invention provides a soil additive comprising a sugar ferment wherein said ferment contains signalling molecules comprising between about 1-50% (w/w) of the organic matter present in the ferment. Preferably the soil additive comprises signalling molecules comprising between about 1-50%, 5-50%, 10-45%, 15-40%, 20-40% (w/w) of the organic matter present in the ferment, 20-30% or 20-25% of the organic matter present in the ferment. The soil additive may contain signalling molecules comprising 1%, 2.5%, 5%, 7.5%, 10%, 15%, 20%, 25%, 30%, 35%, 40%, 45% or 50% (w/w) of the organic matter present in the ferment.

Preferably, the sugar ferment is a molasses ferment, most preferably a molasses ferment comprising between about 20-25% signalling molecules.

The signalling molecules may be intraspecies signalling molecules, interspecies signalling molecules or a mixture of the two. A signalling molecule is a molecule that binds to a membrane receptor and/or moves through the membrane of a cell into the interior of the cell and causes a change in gene expression and/or in metabolism such that adaptive responses to changing conditions or external threats are elicited. Signalling molecules may regulate gene expression at the microbial population and/or community level, leading to changes in activity amongst the members of the population or community. The concept of signalling molecules is discussed, for example, in Cooper (2000) "The Cell: A Molecular Approach." 2nd Ed; Sunderland (Mass.): Sinauer Associates; Signaling Molecules and Their Receptors."

Recently published documents that deal with signalling molecules include: Cirou et al (2012) Appl Env Micro 78:481-492; Brackman et al (2011) PLoS ONE 6: e16084. doi:10.1371/journal.pone.0016084; B Jolivet (PhD Thesis) Synthesis of some furanone derivatives: Putative quorum sensing or chitinase inhibitors (2005); Lahrmann et al (2013) PNAS 110 (34): 13965-13970; and Carter et al (2012) Metab Engin 14: 281-288. These references list a wide range of known signalling molecules, and a skilled reader would understand the types of compounds and chemical entities that are encompassed by the term. Methods to test whether a given compound is a signalling molecule are also provided in the cited documents.

It will be noted that signalling molecules which are quorum quenchers for one order of microbes may be quorum sensors for another order. Furthermore, signalling molecules may be both microbial quorum sensors and/or quenchers and may also be plant elicitors. For example, a biocide to a bacterium can be an elicitor to a fungus. There is functional diversity within the same compound according to its ecological context.

Furthermore, the nature of the compounds which occur as signalling molecules result in a great deal of chemical diversity, and arrange of analogues and orthologues of the compounds identified. A skilled reader would understand that the orthologues and analogues are structurally similar to the identified compounds and may be substituted for those listed. Such analogues and orthologues would preferably function in a similar or identical manner to the identified signalling molecules. In the list of identified signalling molecules provided below, the compounds identified are generally given in terms of classes of compounds, not specific members of such classes. Any specific compounds listed as provided as representatives of the classes identified and merely examples, not a comprehensive list of all signalling molecules identified.

The soil additive comprising a sugar ferment contains organic acids and phenolic compounds. Such compounds are known to be secreted by plant roots to attract beneficial soil microflora. It is believed that the combination of mixed organic acids and phenolics in the soil additive comprising a sugar ferment serves to emulate the way plant roots attract beneficial soil microflora. As such, the signalling molecules of the present invention encompass a range of organic acids and phenolics.

Preferably, the signalling molecules of the soil additive comprising a sugar ferment are selected from one or more of the following groups: microbial quorum sensors and quenchers, biocides or plant elicitors.

Preferably, between 10-50% (w/w) of the signalling molecules are quorum quenchers/sensors, 10-50% (w/w) of the signalling molecules are biocides, and 10-50% (w/w) of the signalling molecules are plant elicitors in the sugar ferment of the present invention. For example, each of the components may provide 10%, 15%, 20%, 25%, 30%, 35%, 40%, 45% or up to 50% of the components, so long as the total comes to 100%. More preferably, about 33% (w/w) of the signalling molecules are quorum quenchers/sensors, 33% (w/w) of the signalling molecules are biocides, and 33% (w/w) of the signalling molecules are plant elicitors in the sugar ferment of the present invention.

Each of the signalling molecules of the soil additive of the present invention may be present at very low amounts, from 1 mg/kg down to as low as 0.1 ng/kg or lower (although detection limits may result in the inability to detect all compounds present). However, the combination of all the signalling molecules in the soil additive may be as high as 500 g/kg, 400 g/kg, 300 g/kg, 250 g/kg, 225 g/kg, 200 g/kg, 175 g/kg, 150 g/kg, 100 g/kg, 75 g/kg, 50 g/kg, 10 g/kg, 1 g/kg, 0.1 g/kg, 50 mg/kg etc.

If the signalling molecules are microbial quorum sensors and quenchers, then preferably the molecules are chosen from the following: furanones, ethanones, peptides and/or sterols.

For example, if the signalling molecules are microbial quorum sensors and quenchers, then the molecules may be chosen from the following: 3(2H)-furanone; dihydro-2-methyl furanone; 2(3H)-furanone; 5-hexyldihydro furanone; ethanone 1-(4-hydroxy-3,5-dimethoxyphenyl) (also called acetosyringone); ethanone 1-(4-hydroxy-3-methoxyphenyl; ethanone 1-(1H-pyrrol-2-yl); benzofuran 2,3-dihydro; and esters of these compounds.

The quorum sensors and quenchers may be chosen from the following: a) AutoInducer 1-mediated quorum sensors and quenchers such as: 2-Furanmethanol 2(3H)-Furanone, dihydro-5-methyl-2-Furancarboxylic acid, ethyl ester 2(3H)-Furanone, 5-ethyldihydro-Benzofuran, 2,3-dihydro-3 (2H)-Benzofuranone, 4,5-dimethyl-Furan, 2,5-diphenyl-7H-Furo[3,2-g][1]benzopyran-7-one, 4,5,6-trimethoxy-Furo[2, 3-H]coumarine, 6-methyl-1-(3-methylphenylamino)-Dihydrofuran-2-one, 4-(3,4-dimethoxybenzyl)-3-(4-hydroxy-3-methoxybenzyl)-Naphtho[2,3-c]furan-1(3H)-one, 3a,4,9,9a-tetrahydro-6-hydroxy-4-(4-hydroxy-3-methoxyphenyl)-7-methoxy-Naphtho[2,3-c]furan-1(3H)-one, or [3aR-(3aα4α,9aβ)]-Naphtho[2,3-c]furan-1(3H)-one; or b) Autoinducer 2-mediated quorum sensors and quenchers such as: Butyrolactone, δNonalactone or 1-Phenyl-2-hexanone.

If the signalling molecules are biocides, then preferably the molecules are chosen from the following: phenols, alcohols, and/or eugenols.

For example, if the signalling molecules are biocides, then preferably the molecules may be chosen from the following: eugenols; phenol 2-methoxy; phenol 4-methyl; phenol 3-ethyl; phenol 4-ethyl; phenol 3,4-dimethoxy; phenol 2-methoxy-4-(1-propyenyl); vanillin. Alternatively, the biocide molecule could be chosen from: Phenol Benzyl Alcohol Phenylethyl Alcohol 4-ethyl-2-methoxy-Phenol, 2,6-dimethoxy-Phenol, Eugenol 3,4-dimethoxy-Phenol, 2-methoxy-4-(1-propenyl)-Phenol, Ethylparaben 4-methyl-Phenol, 2,6-dimethoxy-4(2-propenyl)-Phenol, 4-hydroxy-3,5-dimethoxy-Benzoic acid.

If the signalling molecules are plant elicitors, then preferably the molecules are chosen from the following: ethanones, peptides, higher alcohols, esters, and/or sterols.

For example, if the signalling molecules are plant elicitors, then the molecules may be chosen from the following: ethanone 1-(4-hydroxy-3,5-dimethoxyphenyl) (also called acetosyringone); ethanone 1-(4-hydroxy-3-methoxyphenyl; ethanone 1-(1H-pyrrol-2-yl); benzofuran 2,3-dihydro; 1-butanol,3-methyl; hexadecanoic acid ethyl ester; 1-butanol; 3-methyl-acetate; carbamic acid; methyl-3-methylphenyl ester; and esters of these compounds. Alternatively, the plant elicitor molecule could be chosen from: 1-(1H-pyrrol-2-yl)-Ethanone, 1-(2-hydroxy-6-methoxyphenyl)-Ethanone, 1-(2-hydroxyphenyl)-Ethanone, 1-(4-hydroxy-3-methoxyphenyl)-Ethanone, 1-(2,5-dimethoxyphenyl)-Ethanone, 1-(4-hydroxy-3,5-dimethoxyphenyl)-Ethanone, 2-(1H-imidazo[4,5-b]pyridin-2-yl)-1-(4-morpholyl)-Ethanone.

The peptides that comprise the microbial quorum sensors and quenchers and/or the plant elicitors may be produced by the action of peptidases on the proteins of the microbial biomass that is fermenting the sugar, and/or may be specifically produced directly by the microbial biomass as a result of a stress response due to the fermentation conditions.

Whilst not wishing to be held to any theory, it is believed that compounds in the soil additive such as ethanones (which may also function as plant elicitors) act as quorum quenchers via AutoInducer 1 and AutoInducer 2 pathways respectively, advantageously affecting the soil and plant growth by quenching quorum sensing in lower orders of microbes such as many of the Proteobacteria, Acidobacteria and Bacteriodetes. As a result of the quorum quenching, the growth and/or ecological dominance of lower order microbes is reduced, leading to a more rapid succession to higher orders of microbes. The higher order microbes confer a range of advantages to plant growth, such as root colonization by mycorrhyzal fungi, root endophytes and rhizosphere fungi (which improves nutrient uptake); and root colonization by Actinobacteria (which suppress root diseases).

It is believed that some lower order microbes such as certain Proteobacteria Acidobacteria and Bacteriodetes which use acyl homocysteine lactones as quorum sensors and which are blocked by furanones and related quorum quenchers including ethanones, generally have negative impacts on plant growth. The soil additive of the present invention preferably reduces the growth of such Proteobacteria Acidobacteria and Bacteriodetes and therefore promotes plant growth. Whilst it has been found that some Proteobacteria and Firmicutes are beneficial to plant roots and/or to plant fungi associations, these beneficially Proteobacteria and Firmucutes generally do not rely on quorum sensing to dominate an environment, but rather on symbiotic association which uses its own signalling mechanisms.

It is additionally believed that the complex and higher molecular weight esters in the soil additive advantageously affect the soil by changing the carbon substrate selectivity between the major microbial groups, favouring the high order microbial groups rather than lower order microbial groups. This advantage may be related to the phenomenon of soil priming, with the complex organics of the fermentation mixture providing a boost to the R-strategists over the k-strategists in the microbial population. The esters may function by creating chemical diversity in other active compounds such as furanones, with the esters condensing as side chains on the other compounds and increasing the chemical diversity of those compounds.

The vitamins and proteins produced in the yeast biomass of the soil additive may provide additionally growth factors that contribute to the increased growth of Actinobacteria and Dikarya; it is believe that such higher order microbial groups generally have a positive impact on plant growth.

The soil additive comprising a sugar ferment is preferably produced by fermenting sugar, chosen from the list including but not restricted to: cane sugars and sugar cane processing by-products such as molasses; beet sugar and sugar beet processing by-products such as beet molasses; starch sugars from the hydrolysis of starch, including corn sugar produced by the hydrolysis of corn starch and rice sugar produced by the hydrolysis of rice starch. The sugar used in the fermentation process to produce the soil additive comprising a sugar ferment may be chosen from the list comprising: glucose, fructose, galactose, sucrose, maltose, lactose or mixtures thereof. Preferably, the sugar being fermented is molasses.

The sugar used in the method of the present invention may be a disaccharide, oligosaccharide or polysaccharide or a mixture of two or more sugars.

Anyone reasonably versed in the art will appreciate that, whilst many of the specific examples provided herein use molasses as the sugar feedstock for fermentation, other sources of sugar including refined sugar will achieve the same outcome and are included within the scope of this invention.

The soil additive comprising a sugar ferment is preferably produced by fermenting sugar with a fungi having a budding single cell phase, such as a *Candida* species, an Ascomycete (such as a *Saccharomyces* species) or a Basidiomycete. More preferably the ferment is produced by a yeast, more preferably with *Saccharomyces cerevisciae*. Therefore, the soil additive will further contain microbial biomass, or more preferably yeast biomass. This biomass provides an advantageous source of carbon when the soil additive comprising a sugar ferment is added to soil.

The soil additive may be applied to a soil daily, weekly, monthly, bi-monthly, twice a year, yearly etc as required by the soil. Where the soil additive is being used in an agricultural context, the additive may be applied immediately before sowing of the crop, then re-applied at intervals such as monthly during the growth of the crop and immediately before harvest. Alternatively, the soil additive may be applied in situations such as soil remediation and biomass re-growth. The soil additive may also be added to sand (possibly in conjunction with additional carbon). The soil additive may also be used as an additive to potting mixes. The soil additive may additionally be used in intensive plant growth situations such as greenhouses (where it may be added to the water or liquid substrate of a hydroponics system) or the matrix of vermiculite, perlite, rockwool, coco coir or other non-soil based growth systems and ferticulture systems.

The soil additive may be used to increase the growth of food crops, broad acre crops and vegetable and fruit crops; for land remediation and growth promotion in native bushland; to increase the growth of plants in domestic garden settings and pot plants, and in any other setting where plant growth and increased health is desired.

The soil additive may be applied at a concentration of between about 100 mL to 100 L per hectare, for example 5 L per hectare, 10 L per hectare, 25 L per hectare, 30 L per hectare, 40 L per hectare, 50 L per hectare, 60 L per hectare, 70 L per hectare, 80 L per hectare, 90 L per hectare or 100 L per hectare. For example, it may be applied at between about 2 to 50 L per hectare. Whilst it is preferable to administer the soil additive at a rate of about 5 L per hectare, it is still advantageous to administer the soil additive at a rate of about 100 mL per hectare or more. For example, it may be applied at 200 mL per hectare, 500 mL per hectare, or 1 L per hectare.

The soil additive may be diluted with water or other solvents before application; preferably the additive is dissolved or diluted in water before application to soil. Application may be in the form of a spray applied using a boom spray, or applied to the soil using a hose or jet. Alternatively, the additive may be used in an undiluted form, for example by mixing the undiluted soil additive with a soil or potting mix prior to planting. In a further example of use, the soil additive may be mixed with the aqueous solution being used in a hydroponics set-up.

It is believe that addition of the soil additive of the present invention to soil may lead to increased plant growth through a number of mechanisms occurring in the rhizosphere including: reduced root pathogen pressure, improved nutrient uptake, faster seedling emergence, better rhizosphere colonisation and/or increased mycorrhyzal colonisation. The soil additive may also increase the activity of higher order microbes and reduce the activity and growth of lower order microbes, leading to increased soil carbon sequestration.

Addition of soil additive of the present invention to soil also increases the wetting nature of the soil. It is believed that this is a result of the action of the soil additive comprising a sugar ferment consistently increasing the diversity of Actinobacteria, which are known to metabolise the waxes produced by proteobacteria. Such waxes are produced as a drying-stress response, but by coating soil particles make them non-wetting.

In another embodiment, the invention further provides a method for producing a soil additive comprising the step of:
a) fermenting sugar using a microbe under conditions of high metabolic stress wherein the conditions of high metabolic stress result in production of high levels of signalling molecules by the microbe.

In previous molasses fermentation products, such as those of U.S. Pat. Nos. 3,635,797 and 3,561,944 only about 4% (w/w) of the initial carbon added to the fermentation mixture remained at the end of fermentation, with the majority of the carbon being converted to carbon dioxide and being lost. In contrast, the present invention provides a sugar ferment in which about 50-85% of the initial carbon added to the fermentation mixture remains at the end of fermentation. Of this carbon retained in the sugar ferment, a large percentage is in the form of higher complexity compounds that can act as signalling molecules.

Preferably, the high levels of stress result in a ferment containing signalling molecules comprising between about 1-50% (w/w) of the organic matter present in the ferment. Preferably the soil additive comprises signalling molecules comprising between about 1-50%, 5-50%, 10-45%, 15-40%, 20-40% (w/w) of the organic matter present in the ferment, 20-30% or 20-25% of the organic matter present in the ferment. The soil additive may contain signalling molecules comprising 1%, 2.5%, 5%, 7.5%, 10%, 15%, 20%, 25%, 30%, 35%, 40%, 45% or 50% (w/w) of the organic matter present in the ferment.

Preferably, the sugar is fermented by a fungus having a budding single cell phase, such as a *Candida* species, an *Ascomycete* (such as a *Saccharomyces* species) or a *Basidiomycete*. More preferably the fermentation is carried out by a yeast, more preferably *Saccharomyces cerevisciae*.

The conditions of high metabolic stress may be provided by conditions such as high ionic strength, high osmotic pressure, and anaerobic or oxidative stress (such as that induced by $H_2O_2$). Alternatively, the high metabolic stress may be provided by a combination of two or more of these conditions. Preferably, the high metabolic, stress is provided by a combination of high ionic strength and high osmotic pressure, for example by reducing the water volume in the sugar fermentation reaction.

The high metabolic stress may be produced by imposing high ionic and high osmotic stress conditions, for example by reducing the amount of water in the fermentation mixture to between 0.5× and 4.0×, 0.5× and 2.5×, or 1.0× and 2.0× (v/v) the volume of solids in the fermentation mixture (eg the water can be added to the sugar to create a fermentation mixture comprising two parts water to one part sugar and salts). Alternatively, the high metabolic stress may be produced by imposing high ionic, high osmotic and high oxidative stress conditions, for example by reducing the amount of water in the fermentation mixture to between 1.0× and 4.0× (v/v) the volume of solids in the fermentation mixture and reducing the amount of oxygen or air present during fermentation.

Alternatively, the high ionic strength and/or high osmotic stress can be created by the addition of salt to the fermentation mixture, for example adding sodium chloride to the mixture.

The fermentation is preferably carried out under low oxygen conditions, wherein a small amount of oxygen from air is supplied, sufficient to promote the growth of yeast biomass, but not enough to promote the complete fermentation of the sugars in the sugar source to carbon dioxide. This is preferably achieved by regular, but infrequent aeration and mixing of the fermentation mixture. The reaction may be monitored by measuring the drop in pH and content of sugar. Preferably, the level of air supplied to the fermentation mixture preferably results in an oxygen level of between about 0.1 and 8.5 ppm dissolved $O_2$, for example 0.25 ppm, 1 ppm, 2 ppm, 3 ppm, 4 ppm, 5 ppm, 6 ppm, 7 ppm, 8 ppm, more preferably between about 0.5 and 1 ppm dissolved $O_2$. The air may be added by stirring the fermentation mixture at least one a day, preferably twice a day. Alternatively, the fermentation mixture may be stirred once a day for the first three days, then twice each day until the desired formation end point is achieved and the fermentation reaction is terminated.

The mixture to be fermented by the microbe may also comprise one or more of the following additional ingredients: monopotassium phosphate, magnesium sulphate, urea. Preferably, the monopotassium phosphate is present in an amount between about 0.01 and 1% w/w, for example 0.05%, 0.1%, 0.2%, 0.5%, 0.75% w/w, the magnesium sulphate is present in an amount between about 0.01 and 2% w/w, for example 0.05%, 0.1%, 0.2%, 0.5%, 0.75%, 1.0%, 1.5% w/w and the urea is present in an amount between about 0.01 and 5% w/w, for example 0.05%, 0.1%, 0.2%, 0.5%, 0.75%, 1.0%, 1.5%, 2%, 2.5%, 3%, 4% w/w in relation to the total dry matter of sugar and additional ingredients. More preferably, the mixture to be fermented comprises 0.7% w/w monopotassium phosphate, 1.3% w/w magnesium sulphate and 2.7% w/w urea in relation to the total dry matter of sugar and additional ingredients.

The microbe used to carry out the sugar fermentation may be added to the fermentation reaction at a rate that allows the fermentation reaction to occur in the specific reaction conditions provided. This may mean that more microbe must be added if the reaction conditions are very harsh (eg high osmotic strength etc). For example, the microbe may be added at a rate of between 100 mg/kg and 1000 mg/kg, for example 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, preferably at 500 mg/kg in relation to the total dry matter of sugar and additional ingredients. It has been found that the greater the microbe concentration at the start of the fermentation reaction, the more diverse the resultant product range in relation to esters, furanones etc, and the faster the fermentation occurs. It is advantageous to add increased amounts of microbe if the conditions of high metabolic stress are extremely stressful, eg there are very high levels of ionic stress, osmotic stress or anaerobic or oxidative stress. The increased concentration of microbes at the start of such a fermentation reaction allows the fermentation to occur, despite the adverse conditions.

The fermentation may be carried out for a period of three days to four weeks, or until the sucrose content is at a desired level. For example, the fermentation may be carried out for five days, six days, one week, two weeks or three weeks. Alternatively, the fermentation may be carried out for at least eight weeks, or three, four or five months or longer. The rate of fermentation may be significantly slower as the metabolic stress placed on the microbes fermenting the sugar is increased. Therefore, it is anticipated that the amount of time required to ferment the sugar will vary significantly, for example it may take twice as long to ferment a mixture with twice the osmotic or ionic stress on the microbes.

It may be desirable to terminate the fermentation reaction before all of the sugar, and particularly sucrose, has been removed. However, the fermentation reaction is preferably terminated when the sugar content of the fermentation mixture is approximately 0% or as close to 0% as possible. The presence of sugar, and particularly sucrose, in the fermentation mixture at the end of the fermentation process may lead to problems with cross-contamination and difficulties with long-term storage of the soil additive without undesirable microbial growth. Monitoring of the sugar levels in the fermentation reactor will allow the determination of a suitable timing for fermentation termination according to the needs of the application of the soil additive being produced. Given the slower rate of fermentation occurring as a result of increased metabolic stress, zero levels of sucrose may take some months to achieve if conditions of extreme metabolic stress are placed on the fermentation reaction.

Preferably, the reaction is terminated by the addition of an organic acid such as a tricarboxylic acid (for example citric acid) to the fermentation mixture. Preferably, the organic acid is added at a concentration of between about 1% w/v and 15% w/v, for example 2%, 3%, 4%, 5%, 6%, 7%, 8%, 9%, 10%, 12%, more preferably between about 4% w/v and 10% w/v, most preferably at 5% w/v. Other organic acids including malic acid, oxalic acid and other tricarboxylic acids such as isocitric acid, aconitic acid or trimesic acid could also be used. Preferably, the addition of the organic acid lowers the pH to between 2.3 and 3.7, for example 2.9, 3.0, 3.5, more preferably to about pH 3. The addition of an organic acid promotes the formation of esters which subsequently condense to form higher molecular weight compounds such as decanoic acid. Organic acids also promote the attraction of beneficial soil microbes to plant roots in a manner analogous to the natural secretion of organic acids by plant roots Following termination of the fermentation reaction, it is preferred that urea is added to a concentration which disrupts yeast cell membranes and causes their rupture. For example, the urea may be added at a concentration of between about 1% w/v and 15% w/v, for example 2%, 3%, 4%, 5%, 6%, 7%, 8%, 9%, 10%, 12%, more preferably between about 4% w/v and 10% w/v, most preferably at 5% w/v. Alternatively, the cells can be disrupted by the addition of ammonium sulphate, or other high osmotic stressors that cause cell lysis. The cells may also be ruptured by non-chemical means, such as the use of a French press or other mechanical force, sonic stress, microwaves, heat or high pressure.

In another embodiment of the invention, there is provided a kit for conditioning soil, comprising:
a) soil additive comprising a sugar ferment wherein said ferment contains signalling molecules comprising between about 1-50% (w/w) of the organic matter present in the ferment; and
b) instructions for administration of said soil additive.

In a further embodiment of the invention, there is provided a method for conditioning soil, comprising the step of:
a) adding to the soil an amount of soil additive comprising a sugar ferment wherein said ferment contains signalling molecules comprising between about 1-50% (w/w) of the organic matter present in the ferment.

In a further embodiment of the invention, there is provided a method for promoting plant growth, comprising the step of:
a) adding to the soil an amount of soil additive comprising a sugar ferment wherein said ferment contains signalling molecules comprising between about 1-50% (w/w) of the organic matter present in the ferment.

In a further embodiment of the invention, there is provided a method for increasing crop yield, comprising the steps of:
a) adding to the soil an amount of soil additive comprising a sugar ferment wherein said ferment contains signalling molecules comprising between about 1-50% (w/w) of the organic matter present in the ferment.

In a further embodiment of the invention, there is provided a method for modifying the population composition of rhizosphere microflora, comprising the step of:
a) adding to the soil an amount of soil additive comprising a sugar ferment wherein said ferment contains signalling molecules comprising between about 1-50% (w/w) of the organic matter present in the ferment.

The invention further provides a method for increasing the wetting of a soil, comprising the step of:
a) adding to the soil an amount of soil additive comprising a sugar ferment wherein said ferment contains signalling molecules comprising between about 1-50% (w/w) of the organic matter present in the ferment.

In the above methods, the soil additive comprising a sugar ferment may be generated by the method of fermenting sugar using a microbe under conditions of high metabolic stress wherein the conditions of high metabolic stress result in production of high levels of signalling molecules by the microbe.

Preferably the soil additive comprising a sugar ferment contains signalling molecules comprising between about 1-50% (w/w) of the organic matter present in the ferment. Preferably the soil additive comprises signalling molecules comprising between about 1-50%, 5-50%, 10-45%, 15-40%, 20-40% (w/w) of the organic matter present in the ferment, 20-30% or 20-25% of the organic matter present in the ferment. The soil additive may contain signalling molecules comprising 1%, 2.5%, 5%, 7.5%, 10%, 15%, 20%, 25%, 30%, 35%, 40%, 45% or 50% (w/w) of the organic matter present in the ferment.

Preferably, the sugar ferment is a molasses ferment, most preferably a molasses ferment comprising between about 20-25% signalling molecules.

The soil additive may be applied at a concentration of between about 100 mL to 100 L per hectare, for example 5 L per hectare, 10 L per hectare, 25 L per hectare, 30 L per hectare, 40 L per hectare, 50 L per hectare, 60 L per hectare, 70 L per hectare, 80 L per hectare, 90 L per hectare or 100 L per hectare. For example, it may be applied at between about 3 to 50 L per hectare. Whilst it is preferable to administer the soil additive at a rate of about 5 L per hectare, it is still advantageous to administer the soil additive at a rate of about 100 mL per hectare or more. For example, it may be applied at 200 mL per hectare, 500 mL per hectare, or 1 L per hectare.

The soil additive comprising a sugar ferment may be used to increase the crop yield or improve the plant growth of: commercial and agricultural crops (including cereal crops, vegetable crops, tree plantations, commercial flower growing); home gardens (including both plants in the general soil and indoor and outdoor pot plants); and plants and crops grown in non-soil based situations such as greenhouses growing plants in hydroponics system or matrices of vermiculite, perlite, rockwool, coco coir or other non-soil based growth systems. The soil additive comprising a sugar ferment is of particularly useful application in increasing the plant growth and crop yield of cereal crops such as wheat, oats, barley, rice, maize, sorghum, millet, triticale, or rye.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

As used herein the term "derived" and "derived from" shall be taken to indicate that a specific integer may be obtained from a particular source albeit not necessarily directly from that source.

As used herein, the singular forms "a," "an" and "the" include plural references unless the context clearly dictates otherwise. Thus, for example, reference to a terpene synthase that catalyzes the formation of a terpene includes synthases that catalyze the productions of one or a plurality of terpenes.

Throughout this specification, unless the context requires otherwise, the word "comprise", or variations such as "comprises" or "comprising", will be understood to imply the inclusion of a stated integer or group of integers but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Example 1

Manufacture of a Soil Additive

A series of fermentation mixtures comprising 20 L (28.4 Kg) molasses, 200 g Monopotassium Phosphate, 400 g Magnesium Sulphate and 800 g urea (total 29.8 Kg) were added to six mixing tank reactors which could be sealed from the atmosphere. Either 20 L, 30 L, 40 L, 50 L or 59 L of water (i.e 0.67, 1.006, 1.34, 1.67 or 1.95 times the total weight of solids) were added to the reactors [earlier work on molasses fermentation mixtures by Battistoni (eg U.S. Pat. Nos. 3,561,944; 3,635,797 and CA888164) added water at 2 to 20 times the total weight of raw materials]. After the mixtures were thoroughly blended and dissolved, 10 g of yeast was added to each reactor.

Once each day for the first 3 days, then twice each day for subsequent days, the reactors were opened to the atmosphere and the mixtures stirred, for example by recirculating the mixture through a pump for 10 minutes. This allowed for oxygen to enter the reactors and be stirred through the mixtures.

The fermentation reactions were completed when no more sugar was present in the mix and $CO_2$ production stopped. Citric acid and urea were dissolved in the mixtures to 5% w/v each. The mixtures were then allowed to stand, open to the atmosphere.

Figure 2:
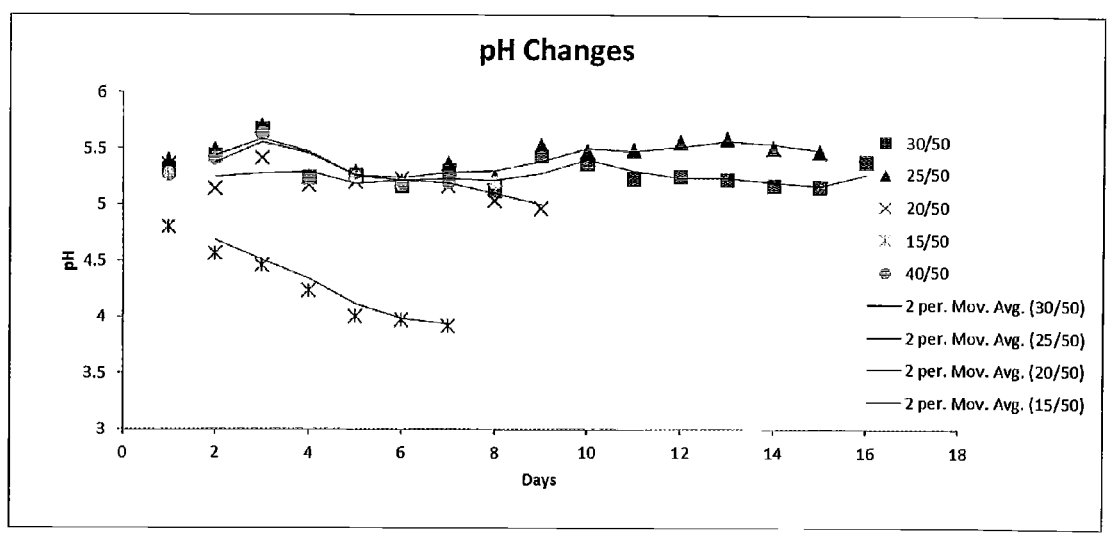
FIG. 2 is a graph of the change in pH during fermentation of a molasses solution according to the present invention over time.

It was found that at the lowest water addition (0.67 v/w), no yeast growth occurred and fermentation did not occur after one week. Yeast growth and fermentation occurred at all higher water addition rates. The progress of fermentation and reduction in organic substrate was monitored by measuring the specific gravity (FIG. 1) and pH (FIG. 2) of the fermentation mixture. A high final specific gravity (ie a final specific gravity of the molasses ferment that is similar to that of the starting fermentation mixture) indicates that there has been a retention of organic matter, specifically in the form of higher complexity compounds that can form signalling molecules.

When fermentations are undertaken at low water concentrations, the mass of organic carbon remaining in solution when the fermentation has completed (as judged by the cessation of carbon dioxide evolution) increases in inverse proportion to the original amount of water added.

This can be measured by comparing the initial specific gravity before yeast is added to the fermentation mix to the final specific gravity once the fermentation reaction is completed.

TABLE 1

Specific gravity comparison

| Molasses/Water (w/v) | Initial SG | Final SG | % of original organics remaining |
|---|---|---|---|
| 28.4/20 | 1.23 | 1.23 | 100% (did not ferment) |
| 28.4/30 | 1.189 | 1.161 | 52% |
| 28.4/35 | 1.157 | 1.090 | 35% |
| 28.4/40 | 1.132 | 1.074 | 14% |
| 28.4/50 | 1.113 | 1.069 | 9% |
| 28.4/59 | 1.090 | 1.041 | 5% |

It was further found that, as fermentation progressed and sugars were oxidised, the osmotic pressure declined and the reaction rate increased. However, it was found that the yeast apparently becomes conditioned to higher osmotic stress. This meant that, after the fermentation has become vigorous, the addition of further molasses to the mixture (such that the osmotic pressure is returned to the starting point), does not result in the expected slowing of fermentation as experienced in the early stages of fermentation, but rather the fermentation proceeds at a similar rate to before the additional molasses was added.

As discussed, various fermentation mixtures were tested, with differing amounts of water added to 20 L of molasses for the fermentation. Post fermentation, all batches were made up to 100 L, thus have the same starting mass of molasses and final mass of salts. Table 2 provides the percentage of total organics provided by that compound. Organic components were generally about 15% by weight of the final product, with signalling molecules comprising between about 20-25% of the organic matter present in the ferment.

TABLE 2

Component analysis of molasses ferment

| | Ferment (kg molasses/L water) | | | | |
|---|---|---|---|---|---|
| | 28.4/30 g/L | 28.4/35 g/L | 28.4/40 g/L | 28.4/50 g/L | 28.4/59 g/L |
| Examples of quorum quenchers/sensors | | | | | |
| Furanone (3(2H) dihydro-2-methyl | 34.1 | 20.7 | 1.79 | 0.945 | 0.285 |
| Furanone 2(3H) 5-hexyldihydro | 0.211 | 3.15 | 1.54 | 0.279 | 0.145 |
| Acetosyringone | 31.8 | 31.2 | 4.56 | 2.19 | 1.16 |
| Ethanone 1-(1H-pyrrol-2-yl) | 24.7 | 9.52 | 0.322 | 1.09 | 0.305 |
| Benzofuran 2,3-dihydro- | 51.1 | 27.2 | 0.252 | 0.108 | 0.105 |
| Ethanone 1-(4-hydroxy-3-methoxyphenyl) | 5.82 | 22.75 | 3.69 | 2.02 | 0.815 |
| Examples of bacteriocides | | | | | |
| Phenol 3-ethyl | 5.51 | 157 | 38.8 | 40.5 | 19.2 |
| Phenol 4-ethyl | 13.2 | 107 | 12.1 | 1.32 | 0.12 |
| Phenol 3,4-dimethoxy | 50.4 | 3.99 | 10.5 | 5.17 | 0.76 |
| Phenol 2-methoxy-4-(1-propenyl) | 0.12 | 2.48 | 0.291 | 0.013 | 0.002 |
| Benzoic acid | 58.2 | 26.6 | 0.462 | 1.26 | 0 |
| Examples of Plant Elicitors | | | | | |
| Eugenol | 6.26 | 1.71 | 4.42 | 0.12 | 0.06 |
| Vanillin | 0.16 | 3.72 | 8.41 | 3.12 | 0.87 |
| Quinoline | 0.03 | 0.15 | 1.18 | 0.91 | 0.17 |
| Acetosyringone | 31.8 | 31.2 | 4.56 | 2.19 | 1.16 |
| Ethanone 1-(4-hydroxy-3-methoxyphenyl) | 5.82 | 22.75 | 3.69 | 2.02 | 0.815 |
| Ethanone 1-(1H-pyrrol-2-yl) | 24.7 | 9.52 | 0.322 | 1.09 | 0.305 |

Table 2 shows the concentration of different functional groups of compounds produced at different levels of osmotic stress during fermentation. The components were measured at the end of fermentation, when $CO_2$ production had ceased for each different fermentation condition, and water was added to give a final volume of 100 L.

From Table 2 it can be seen that almost all signalling molecules (including microbial quorum sensors and quenchers, biocides and plant elicitors) increase in concentration as osmotic/ionic stress increases. Furthermore, generally as osmotic/ionic stress increases the compounds in the same class (quorum sensors/quenchers, biocides and plant elicitors etc) get bigger and more complex, and further they become more aromatic than aliphatic (i.e. benzene and phenol derivatives start to predominate).

Given that simple microbial groups tend to grow better on simple substrates, whereas higher order microbes can metabolise the more complex compounds, these observations support the position that the fermentation of molasses under stress conditions produces substrates which selectively favour the growth of higher microbial orders.

The analysis of the fermentation mixture was carried out by GC/MS/MS. It would be clear to a skilled reader that many of the components will interact in solution, and that the compounds detected in molasses ferment will only represent some of the many compounds present in the mixture due to both degradation or condensation of the complex compounds and the limitations of GC/MS/MS detection.

Example 2

Use of Soil Additive

Wheat growth trials were undertaken at Forrestdale, Western Australia, on an area which was cleared, but had been unused for 10 years. One series of beds (Trial 1) were treated to increase soil organic matter and fertility by spreading compost at 80 cubic meters per hectare, with the material incorporated into soil using a rotary hoe. Another series of beds (Trial 2) had no such treatment, but were cultivated by rotary hoe. Trial 1 was sown on 2 Apr. 2012, and Trial 2 was sown on 7 May 2012.

After soil treatments, soil was sampled from each bed and analysed. The bed treated with compost had organic carbon of 4.2%, and Colwell extractable phosphate of 32 mg/kg. The bed without added compost had organic carbon at 0.38% and Colwell extractable phosphate at 8.1 mg/kg.

Each area was divided into 5 beds of 1×1 m, making a total of 10 beds, of which 5 had relatively high fertility and organic matter and 5 had low fertility and organic matter.

Wheat of the Wyalkatchem variety was sown in 5 rows, 180 mm apart with seeds 25 mm apart in each row. On the day of sowing, beds were treated with molasses ferment derived from fermenting 20 L of molasses in 50 L of water in accordance with Example 1 (hereafter referred to as "20/50 ferment"). The 20/50 ferment was applied at rates equivalent to 2, 4, 6 and 16 L per hectare, by diluting the appropriate amount of 20/50 ferment in 8 L of water, and applying it to beds using a watering can. In both compost treated and untreated areas, one control bed did not have 20/50 ferment applied, but had 8 L of water applied. Beds were re-treated with the same ferment application rates (or with water) 20 days later, when seedlings had developed to the two leaf stage.

After 5-6 days, when the first emergent seedlings were evident, the count for emerging seedlings for each treatment was measured over 48 hours.

Four times during plant growth, 10 plants were sampled randomly from each treatment by carefully digging the entire plants from beds, including roots and adhering soil. At each sampling plant tops from each treatment were individually dried in an oven to determine dry weight, then digested to determine leaf tissue nutrient status. Soil adhering to roots was collected, dried and rhizosphere DNA was extracted. Roots were washed and stained to determine mycorrhizal colonisation.

At the completion of trials in November grain heads were harvested for determination of grain yield.

Seedling Emergence

Figure 3A:
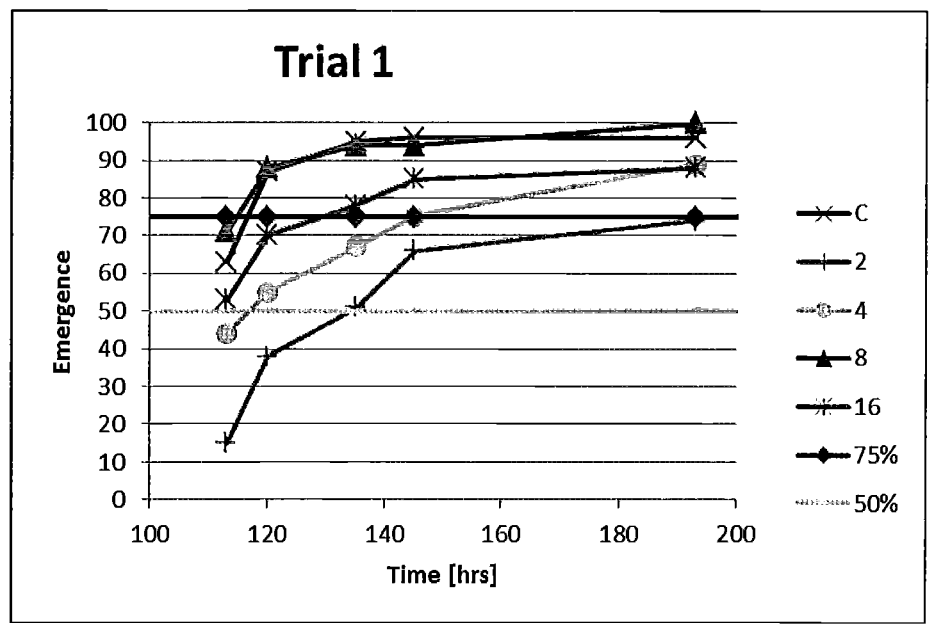
FIGS. 3A and 3B are graphs of the number of emergent seedlings at day 5-6 in high organic matter (Trial 1) and low organic matter (Trial 2) plots treated with 20/50 ferment.
Figure 3B:
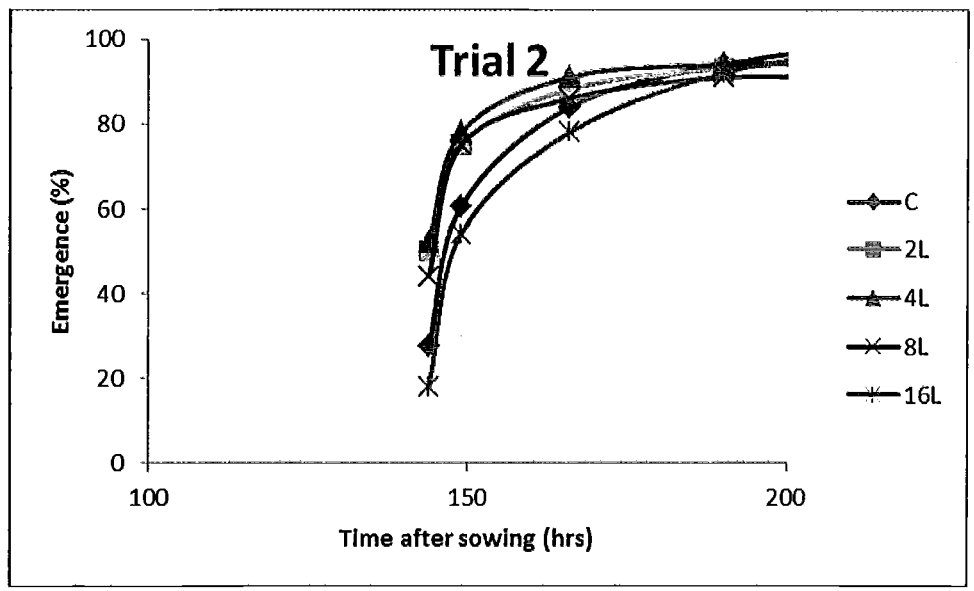

At day 5-6, seedling emergence was counted over 48 hours (FIGS. 3A and 3B).

In the higher fertility soil (Trial 1) there was no clear pattern of impact of ferment application on seedling emergence. In the lower fertility soil (Trial 2), application of the 20/50 ferment at 2, 4 and 8 L/ha promoted faster seedling emergence compared to controls and beds treated with 16 L/ha.

Plant Dry Weight

Figure 4A:
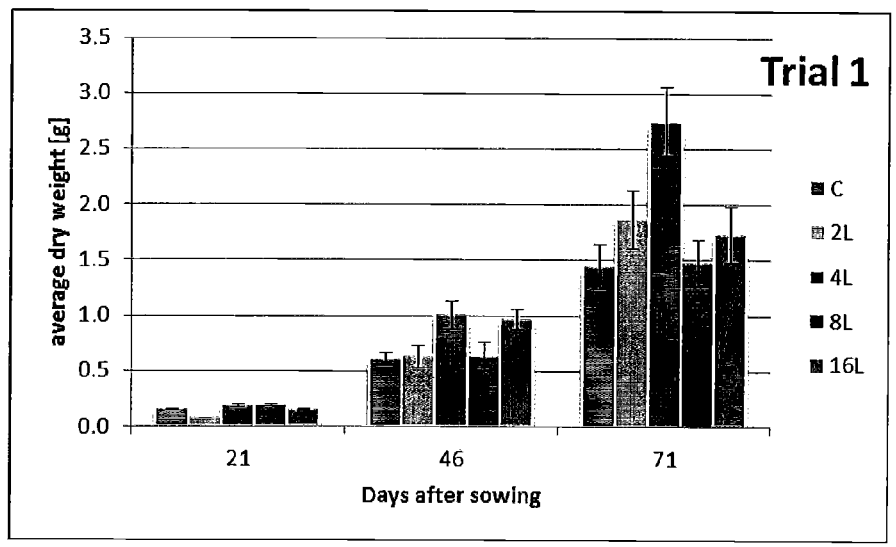
FIGS. 4A and 4B are graphs of the plant dry weight in high organic matter (Trial 1) and low organic matter (Trial 2) plots treated with 20/50 ferment.

In Trial 1, significantly greater plant dry weight was evident by day 46 after sowing, particularly in plants treated with 4 and 16 L/ha of ferment. By day 71, dry weight in plants treated with 4 L/ha had nearly doubled compared to controls (FIG. 4A).

Figure 4B:
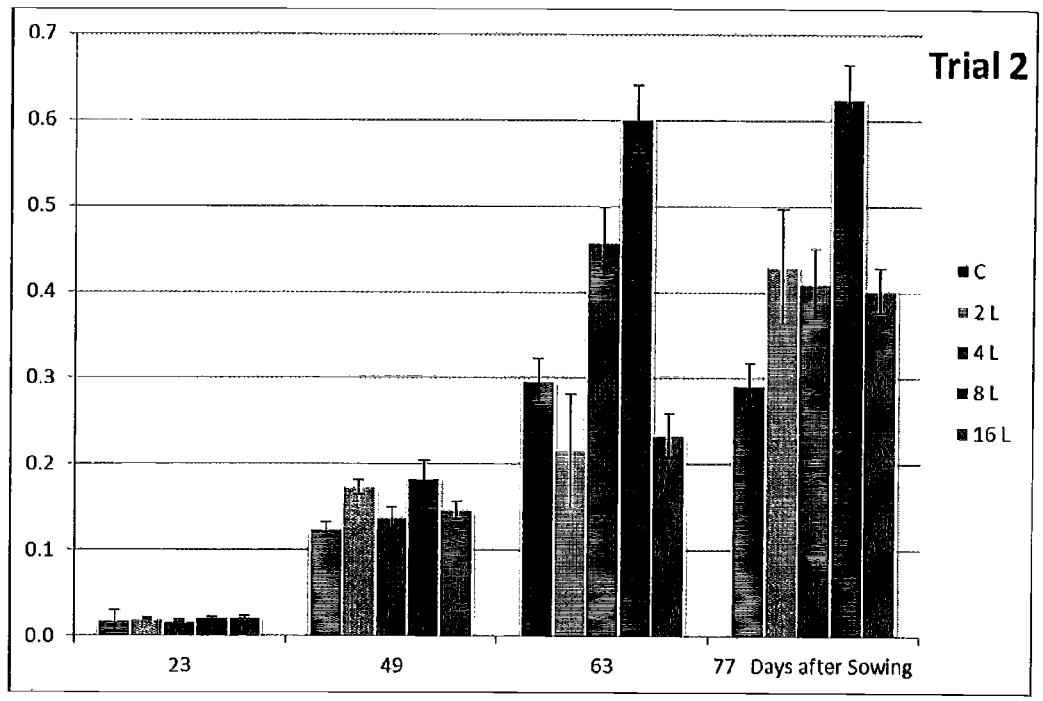

In Trial 2, dry weight gain with ferment treatment was again apparent, but the pattern was complex, with small differences at day 49 after sowing, but then larger differences for treatment rates of 4 and 8 L/ha at day 63 (FIG. 4B).

At day 77, all ferment treatments produced higher dry weight than controls.

Nutrient Leaf Tissue Levels

Nutrient leaf tissue levels were determined by the method of Jones J. B. and Steyn W. J. A (1973) Sampling, handling and analysing plant tissue samples. In "Soil Testing and Plant Analysis (Eds Walsh L M and Beaton J D), Soil Sci. Soc. Am: Madison).

Figure 5A:
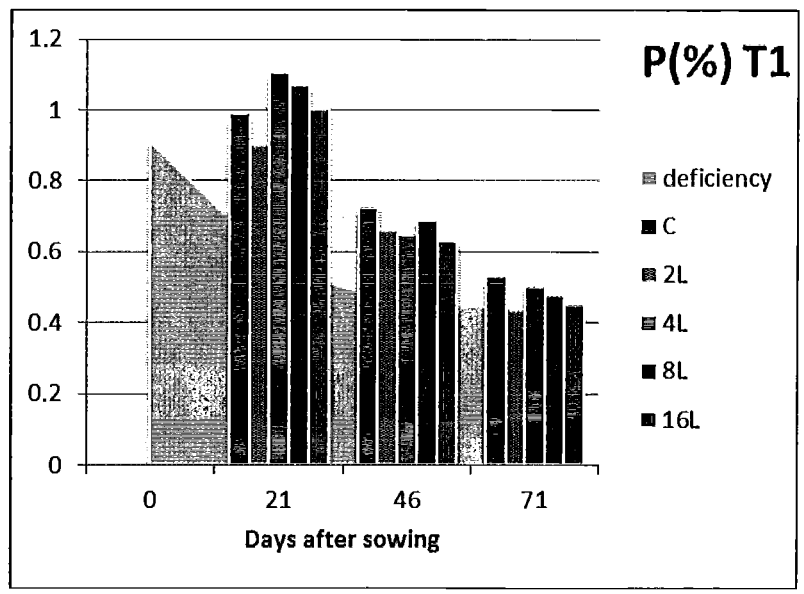
FIGS. 5A-5D are graphs showing the levels of N and P in leaf tissue collected from plots with high organic matter (Trial 1) and low organic matter (Trial 2) treated with 20/50 ferment.
Figure 5B:
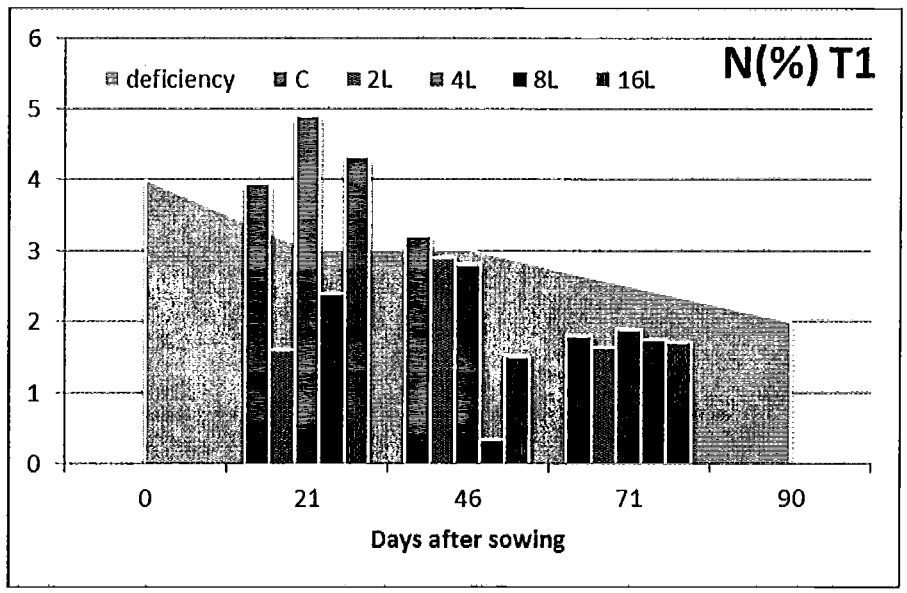

In Trial 1 where abundant nutrients were available, plants from all treatments had sufficient leaf tissue phosphate to conclude availability of this nutrient did not limit growth. Leaf tissue Nitrogen showed a complex pattern, with greater levels at day 21, but general decline thereafter suggesting Nitrogen availability may have been limiting growth rates (FIGS. 5A and 5B).

Figure 5C:
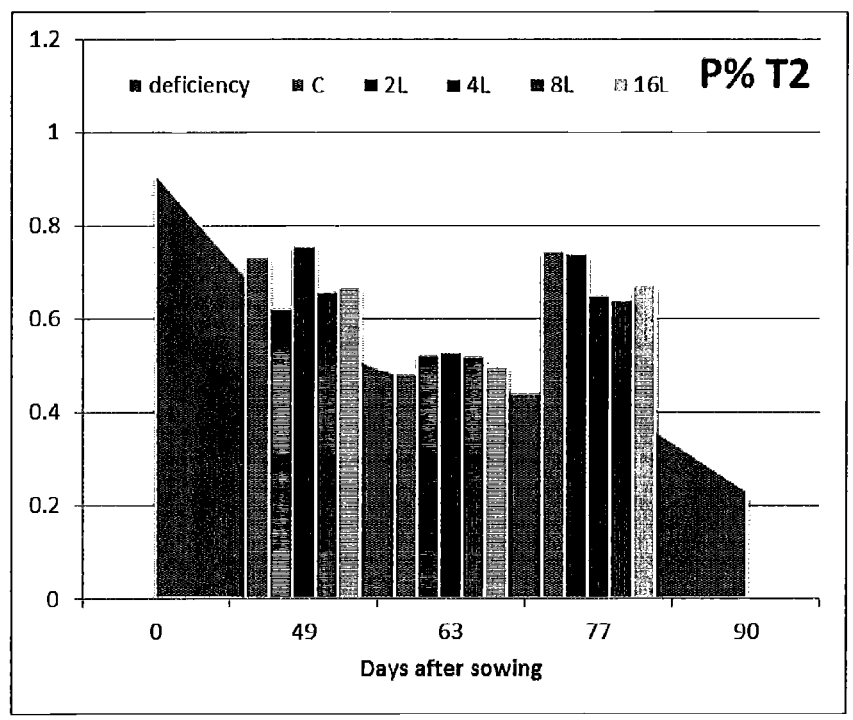
Figure 5D:
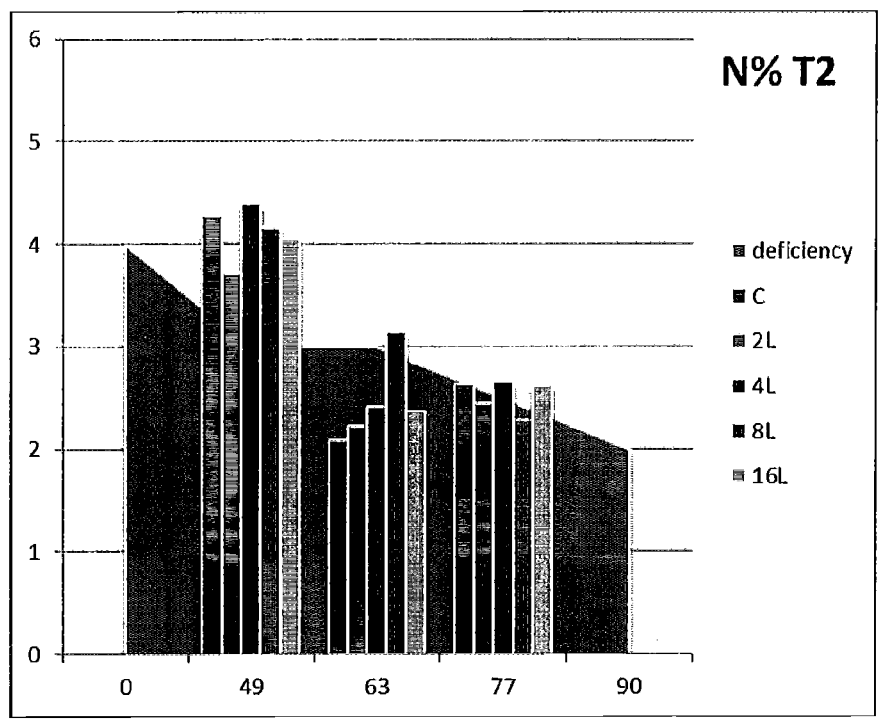
Figure 6A:
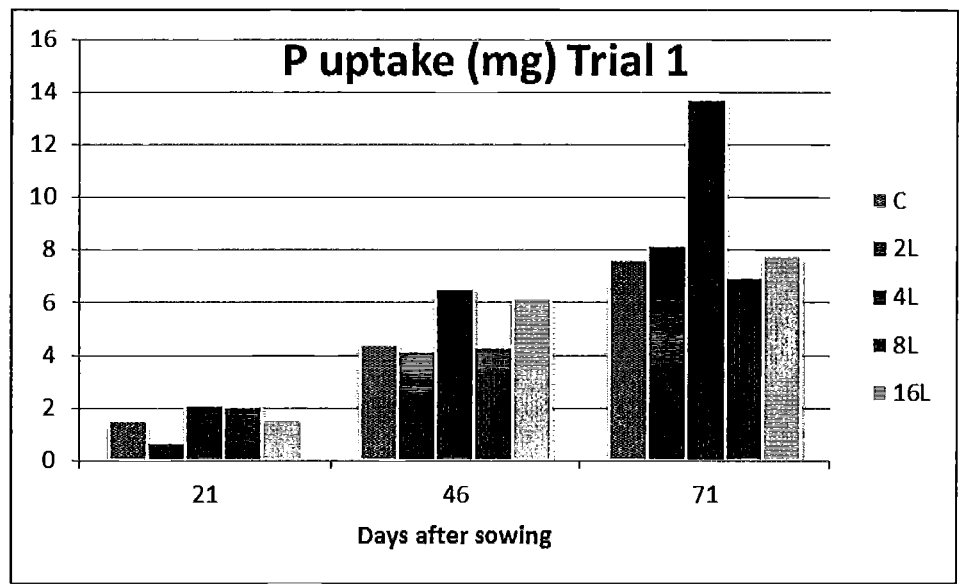
FIGS. 6A-6D are graphs showing the levels of N and P uptake by plants in plots with high organic matter (Trial 1) and low organic matter (Trial 2) treated with 20/50 ferment.
Figure 6B:
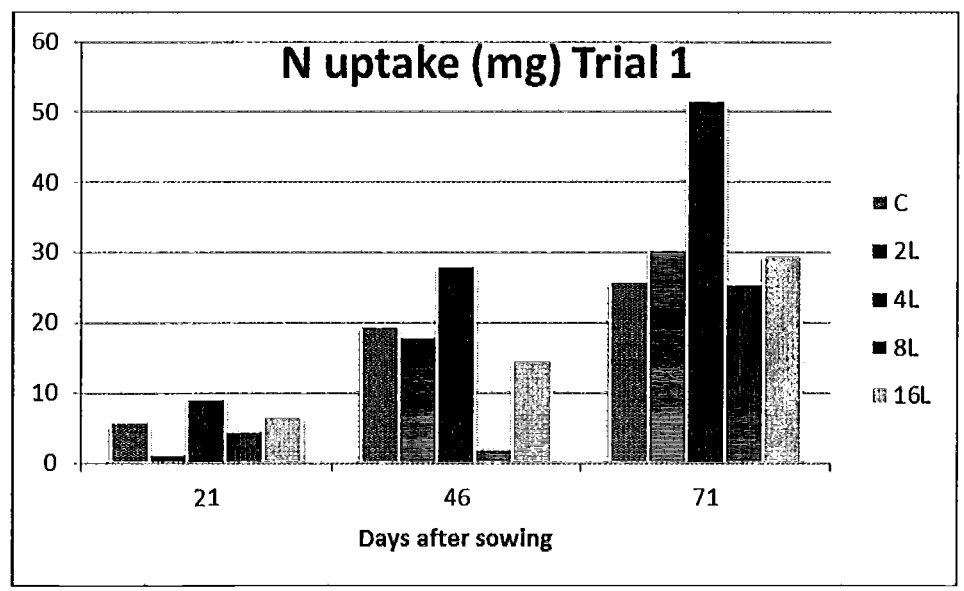
Figure 6C:
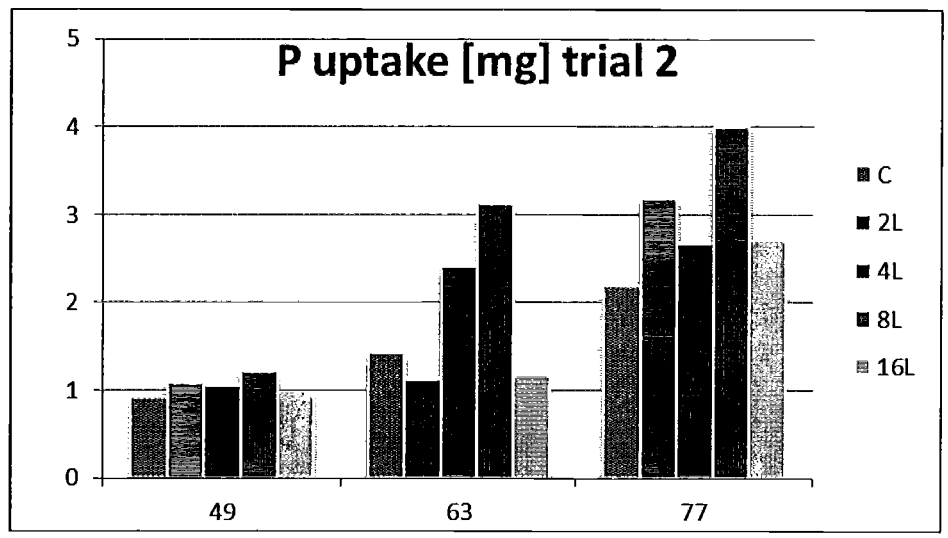
Figure 6D:
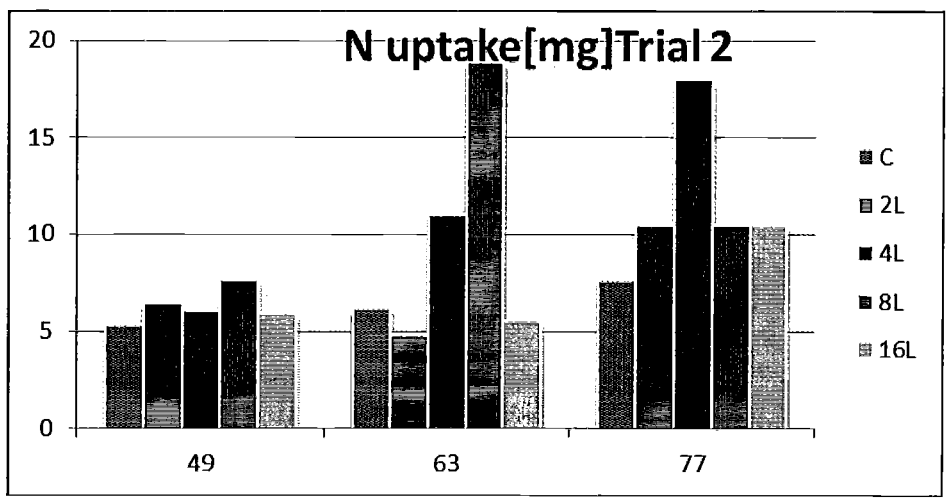

In Trial 2 with lower nutrient availability in soils, again leaf tissue phosphate levels were above levels which might cause nutrient limitation, whereas nitrogen was in the range where its availability could limit growth rates (FIGS. 5C and 5D).

Nutrient Uptake

The nutrient uptake rates were determined by multiplying the dry weight of tissue by the proportion of each element.

In the higher fertility soil of Trial 1, ferment application at 4 L/ha promoted the greatest uptake of N and P, whereas in the lower fertility soils of Trial 2, 4 and 8 L/ha application rates promoted the greatest nutrient uptake (FIGS. 6A-6D).

When considered in the context of plant dry weight and nutrient levels, it is evident that the application of 20/50 ferment promoted greater nutrient uptake per plant for nitrogen and phosphorus in both high and low nutrient available soil compared to control soils where no 20/50 ferment had been applied.

Mycorrhyzal Colonisation

Mycrorhyzal scoring was carried out according to Brundett, M Bougher, N et al (1996) *Working with Mycorrhizas in Forestry and Agriculture*. Canberra ACAIR Monographs.

Figure 7A:
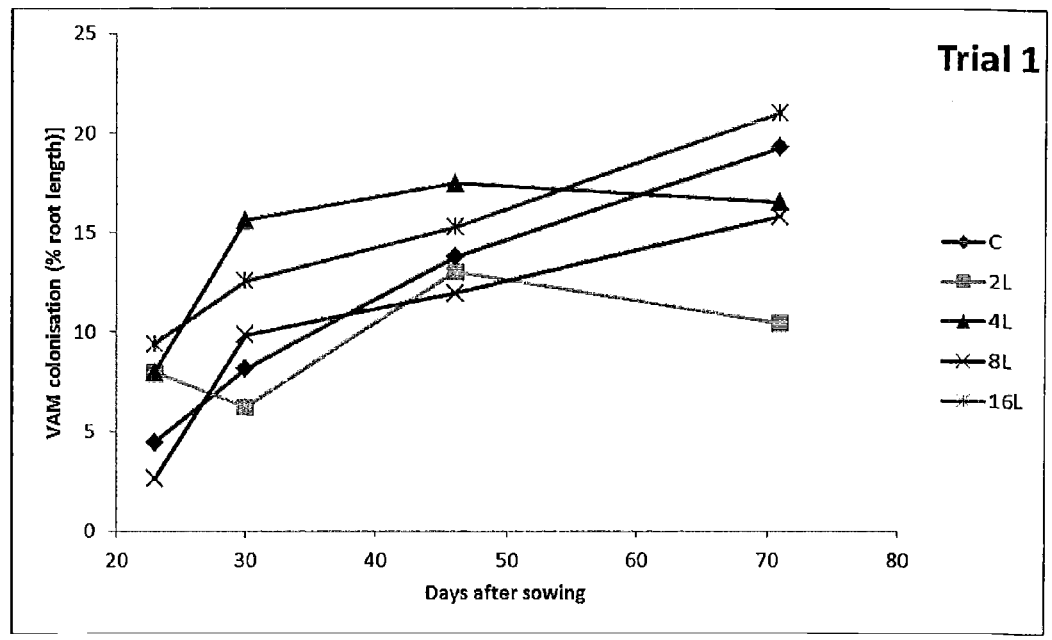
FIGS. 7A and 7B are graphs of the VAM colonisation on roots of plants grown in high organic matter (Trial 1) and low organic matter (Trial 2) plots treated with 20/50 ferment.

In Trial 1, the extent of root colonization by vesicular arbuscule mycorrhyzal (VAM) did not show any impact of ferment treatment (FIG. 7A).

Figure 7B:
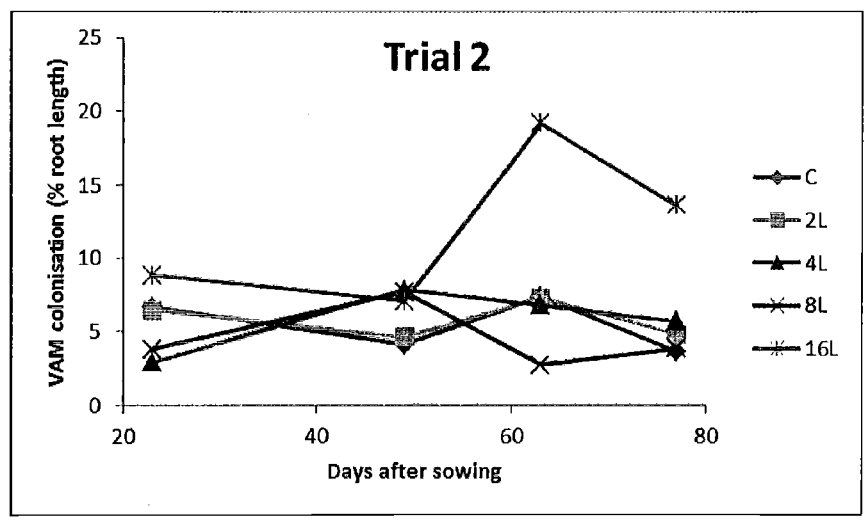

In Trial 2, VAM colonisation was generally much lower, but the treatment of beds with 20/50 ferment at 16 L/ha promoted increased colonisation (FIG. 7B).

Grain Yield

On 15 Oct. 2012 for Trial 1 and 18th November for Trial 2, 25 plants from each treatment had grain heads harvested, grain separated from chaff and weighed. The yield per hectare was calculated based on the weights measured.

TABLE 3

| | Grain Yield | |
|---|---|---|
| Treatment | Yield Trial 1 (t/ha) | Yield Trial 2 (t/ha) |
| Control | 2.16 | 1.52 |
| 2 L/ha | 2.21 | 2.91 |
| 4 L/ha | 2.69 | 2.02 |
| 8 L/ha | 3.12 | 2.45 |
| 16 L/ha | 2.41 | 2.09 |

The harvest results show that at all application rates of 20/50 ferment, an increased grain yield was achieved. In Trial 1, a maximum 44% yield increase was achieved at application rates of 8 L per hectare, whilst a 25% increase was achieved at application rates of 4 L/ha.

In Trial 2 the relative increase of treated beds to controls in grain yield was higher, with the maximum yield increase of 91% achieved with an application rate of 2 L/ha. Again all treated beds had higher grain yield than controls.

Application of the 20/50 fermentation product meant low fertility soils became as productive as high fertility soils without fermentation product treatment, and higher fertility soils became even more productive.

Microbial Profiling

Soil samples from each plot were dried at 40° C. in a vacuum oven and put through a 1 mm sieve to remove larger particles. The soil was then ground in a bead mill to produce a particles size of <200 microns. DNA was extracted from a 500 mg subsample of ground soil using the PowerSoil® DNA Isolation kit (MoBio, USA). The manufacturer's instructions were modified by using a Qiagen Retsch Tissuelyser MM301 (Qiagen, USA) at 25 Hz for 20 min.

ARISA has been previously described by (Fisher & Triplett, 1999) and relies on the length heterogeneity of intergenic transcribed spacer (ITS) regions between the 16S and the 23S rRNA genes in the rRNA operons.

Six primer pairs were used to amplify the intergenic spacer regions for the ARISA assays, each primer pairs amplified a major soil taxonomic group encompassing agricultural soil in Western Australia. Three primer sets were used to amplify the 16S-23S rRNA ITS regions for soil bacterial communities (named Bac I, Bac II and Bac III, including but not exclusive to Alpha proteobacteria, Beta proteobacteria and Firmicutes respectively). These primer pairs were ITSF/ITSReub (Cardinale et al., 2004), S-D-Bact-1522-b-S-20/L-D-Bact-132-a-A-18 (Ranjard et al., 2001) and 1406F/23Sr (Fisher & Triplett, 1999). The Archaeal microbial community was amplified using the A751F/UA 1406R (Baker, Smith, & Cowan, 2003) primer pair, the Actinobacterial community was amplified using the primers SpF/SpR (Mazza, Monciardini, Cavaletti, Sosio, & Donadio, 2003) primer pair and the Dikarya fungal microbial community was amplified using the ITS1-F/ITS4 (Rooney & Clipson, 2009). The forward primer for each primer pair was fluorescently labelled with FAM (6-carboxyrhodamine) phosphoramidite dye fluorochromes (GeneWorks, South Australia) and the sequences for each are shown below in Table 4.

TABLE 4

ARISA Primer Sequences

| Primer Name (5'-3') | Primer Sequence | SEQ ID NO |
|---|---|---|
| ITSF (Bac I) | 5GT CGT AAC AAG GTA GCC GTA | 1 |
| ITSReub (Bac I) | GCC AAG GCA TCC ACC | 2 |
| SD-Bact-1522-b-S-20 (Bac II) | 5TG CGG CTG GAT CCC CTC CTT | 3 |

TABLE 4-continued

ARISA Primer Sequences

| Primer Name (5'-3') | Primer Sequence | SEQ ID NO |
|---|---|---|
| LD-Bact-132-a-A-18 (Bac II) | CCG GGT TTC CCC ATT CGG | 4 |
| 1406F (Bac III) | 5TG YAC ACA CCG CCC GT | 5 |
| 23sR (Bac III) | GGG TTB CCC CAT TCR G | 6 |
| A751F (Archaea) | 5CC GAC GGT GAG RGR YGA A | 7 |
| UA1406R (Archaea) | ACG GCG GT GWG TRC AA | 8 |
| SpF (Actinobacteria) | 5TA CCG GAA GGT GCG G | 9 |
| SpR (Actinobacteria) | GGG TAC TGA GAT GTT TCA CTT C | 10 |
| ITS1-F (Dikarya Fungi) | 5CT TGG TCA TTT AGA GGA AGT AA | 11 |
| ITS4-R F (Dikarya Fungi) | TCCTCC GCT TAT TGA TAT GC | 12 |

DNA amplifications were performed in a final volume of 20 μl, containing 1.0 U of Taq DNA polymerase, 1×PCR buffer and 1.0 mM of each dNTP (Fisher Scientific, Western Australia). Each PCR underwent optimisation and therefore the concentrations of the primers and the $MgCl_2$ varied. The optimised PCR conditions and concentrations are shown in Table 5.

TABLE 5

Optimised PCR conditions, primers and $MgCl_2$ concentrations

| | ITSF/ ITSReub | S-D-Bact-1522-b-S-20/L-D-Bact-132-a-A-18 | 1406F/ 23Sr | A751F/UA 1406R | SpF/SpR | ITS1-F/ ITS4 |
|---|---|---|---|---|---|---|
| Primer Conc. (μl) | 10 | 10 | 20 | 10 | 10 | 20 |
| MgCl2 (mM) | 3 | 2.5 | 3.1 | 3 | 2.5 | 2.4 |
| PCR Conditions | 3 min at 94 C. (45 s at 94 C., 45 s at 55 C., 45 s at 72 C.) × 35 cycles 5 min at 72 C. Hold at 4 C. | 3 min at 94 C. (45 s at 94 C., 45 s at 55 C., 45 s at 72 C.) × 35 cycles 5 min at 72 C. Hold at 4 C. | 3 min at 94 C. (45 s at 94 C., 45 s at 55 C., 45 s at 72 C.) × 35 cycles 5 min at 72 C. Hold at 4 C. | 5 min at 94 C. (30 s at 94 C., 45 s at 55 C., 30 s at 72 C.) × 35 cycles 5 min at 72 C. Hold at 4 C. | 5 min at 94 C. (1 m at 94 C., 1 m at 55 C., 2 m at 72 C.) × 35 cycles 10 min at 72 C. Hold at 4 C. | 5 min at 94 C. (45 s at 94 C., 45 s at 55 C., 45 s at 72 C.) × 40 cycles 5 min at 72 C. Hold at 4 C. |

Upon amplification, 1 ml of HiDi formamide (Applied Biosystems, USA) was mixed with 6 μl of internal size standard LIZ 1200 (Applied Biosystems, USA). A 19 μl aliquot of this mixture was added to each well and to this, 1 μl of each PCR product was mixed. The samples were then analysed using an ABI 3730 automated sequencer (Applied Biosystems, USA). Using the LIZ 1200 size standard, fragments smaller than 20 bp and larger than 1200 bp were excluded. GeneMapper software (Applied Biosystems, USA) was used to determine the peak area, height and size of the peaks present for each sample. The background fluorescence threshold was manually set at 100 relative fluorescence units for all samples.

The scores for each primer pair represent the number of AFLP signals greater than 100 RFU's using the ABI 3730 automated system. Such signal strength occurs when those taxa were present in numbers likely to be greater than $10^4$ microbes per gram of soil.

Rhizosphere Microflora

Analysis of DNA collected throughout the growing season from plant rhizosphere shows there is a relative reduction in the diversity and dominance of bacteria belonging to the beta proteobacteria, and an increase in the number of dominant taxa belonging to the dikarya.

The complexity of rhizosphere microflora as revealed by ARISA is manifest in there being in excess of 500 different organisms present in the soil surrounding roots. The vast majority of these are present in only small population levels, thus are considered non-dominant taxa (FIG. 8C).

Figure 8A:
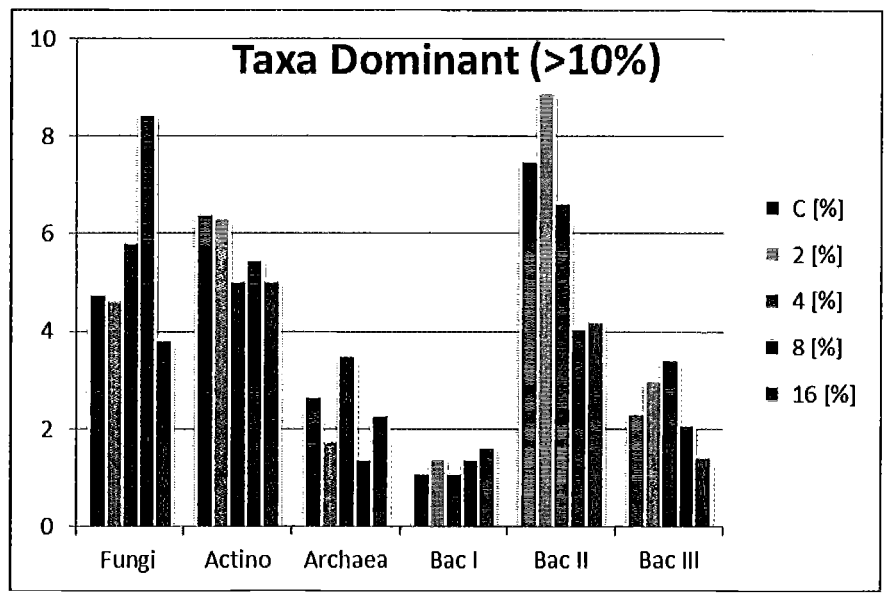
FIGS. 8A-8C are graphs of the relative abundance of six major organism groups colonising the roots of plants grown in high organic matter (Trial 1) and low organic matter (Trial 2) plots treated with 20/50 ferment.
Figure 8B:
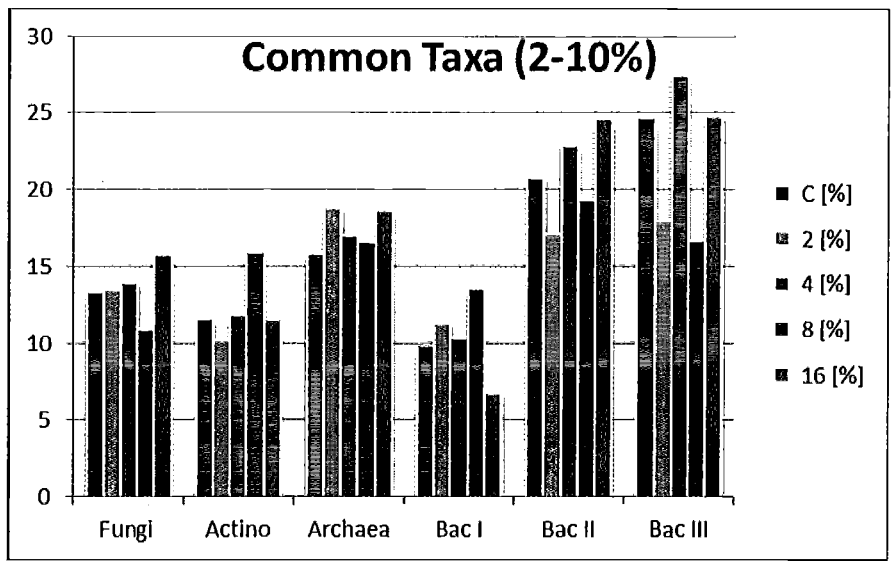
Figure 8C:
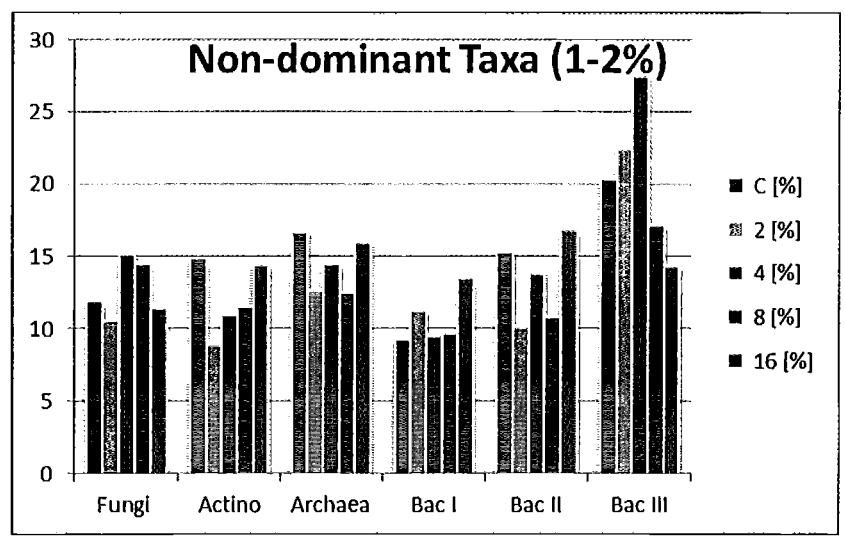

When considering only those taxa present at greater than 2% of the biomass for that particular group (of the six groups measured), the influence of the application of the fermentation product becomes clearer (FIGS. 8A and 8B).

Example 3

Use of Soil Additive

Wheat rhizosphere soil was compared across plots with and without Bioprime 20/50 ferment addition using the ARISA assay as described above. The experiment was carried out near Buntine, Western Australia, and consisted of 72 plots 10 meters by 2 meters, each of which was randomly assigned to one of 24 factorial treatments. There were three treatment types: control (no additives); 20/50 ferment added at low (2 L/ha) or high (4 L/ha) rates; and urea nitrogen fertilizer added at a rate of 45 kg/ha at seeding, 22 kg/ha at seeding and 22 kg/ha at tillering, or 45 kg/ha at tillering. Plots were sown with Mace variety of wheat on 30 May 2013, treatments were applied on the same day, and soil was sampled on 29 Jun. 2013.

ARISA microbial diversity assays estimate the number of microbial species in a soil sample by measuring the number of sequence length variants across the nuclear internal transcribed spacer (ITS) region, a region of DNA which is highly variable in sequence between different species (Fisher & Triplett, 1999). Sequence length variants are considered to be different operational taxonomic units (OTUs), and the number of OTUs measured by ARISA in a soil sample is positively related to, but not exactly the same as, the actual number of microbial species in that sample. The ITS region lies between the small and large subunit nuclear ribosomal RNA genes (rRNA genes), which are more similar in DNA sequence between species than the ITS region (Woese and Fox 1977). The ARISA assay can therefore be targeted to specific groups of microbes (eg. firmicute bacteria, fungi) by utilising a pair of primers that are specific to the conserved rRNA genes surrounding the ITS region for that group, and which therefore amplify the ITS region only for that group (Fisher & Triplett 1999). In our ARISA assay for specific groups of bacteria, we utilise a reverse primer common to all bacteria, but identified a highly specific forward primer in each case.

Soil samples from each plot were collected in the field, placed on wet ice, returned to the laboratory, and stored at $-20°$ C. prior to analysis. Soil samples were thawed on wet ice, hand homogenised, and 0.25 g subsamples taken. Total DNA was extracted from subsamples using the PowerSoil DNA Isolation kit (MoBio, Carlsbad, USA), following manufacturer's instructions except that samples were lysed using a TissueLyserII (Qiagen, Hilden, Germany) at 25 Hz for 20 minutes, and we modified the amount of lysed extract used in subsequent downstream purification (to 50-500 µl) depending on the average level of organic contamination in each batch of samples.

Ten primer pairs were used to amplify across the ITS region, corresponding to the groups of microbes shown in Table 6 below.

TABLE 6

Details of groups targeted, primers used, and assay conditions in the ARISA assays.

| Group Target | Primer Codes (forward/ reverse) | Sequences (forward/reverse) | Fluorescent Label (forward) | $MgCl_2$ Concentration in PCR (mM) | Post-PCR Multiplex Pool | Reference | SEQ ID NO |
|---|---|---|---|---|---|---|---|
| Bacteria I | ITSF | GTCGTAAACAAGGTAGC CGTAGCCAAGGCATCCA CC | 5'-6FAM | 3.0 | 1 | Cardinale et al 2004 | 1 2 |
| Firmicutes | 1040firmRCF ITSR | GACAGGTGGTGCATGGT GCCAAGGCATCCACC | 5'-VIC | 2.5 | 1 | De Gregoris et al 2011, 2012 | 13 2 |
| Actinobacteria | act920F3 ITSR | TACGGCCGCAAGGCTAG CCAAGGCATCCACC | 5'-NED | 3.125 | 1 | De Gregoris et al 2011, 2012 | 14 2 |
| Bacteria III | 1406F 23sR | TGYACACACCGCCCGTG GGTTGCCCCATTCRG | 5'-6FAM | 3.125 | 2 | Fisher & Triplet 1999 | 5 6 |
| Gamma Proteobacteria | G1202RCF ITSR | CATCATGGCCCTTACGG CCAAGGCATCCACC | 5'-VIC | 2.5 | 2 | De Gregoris et al 2011, 2012 | 15 2 |
| Archaea | A751F UA1406R | CCGACGGTGAGRGRYGA AACGGGCGGTGWGTRCA A | 5'-PET | 3.0 | 2 | Baker et al 2003 | 16 8 |
| Dikaryotic Fungi | ITS1F ITS4R | CTTGGTCATTTAGAGGA AGTAATCCTCCGCTTAT TGATATGC | 5'-6FAM | 2.5 | 3 | Rooney & Clipson 2009 | 11 12 |

TABLE 6-continued

Details of groups targeted, primers used, and assay conditions in the ARISA assays.

| Group Target | Primer Codes (forward/ reverse) | Sequences (forward/reverse) | Fluorescent Label (forward) | MgCl$_2$ Concentration in PCR (mM) | Post-PCR Multiplex Pool | Reference | SEQ ID NO |
|---|---|---|---|---|---|---|---|
| Acidobacteria | acidoG1_8.1F ITSR | GAACCTTACCTGGGCTC GAAAGCCAAGGCATCCA CC | 5'-PET | 2.5 | 3 | Gans et al 2012 | 17 2 |
| Bacteriodetes | cbf967RCF ITSR | ATACGCGAGGAACCTTA CCGCCAAGGCATCCACC | 5'-NED | 3.125 | 3 | De Gregoris et al 2011, 2012 | 18 2 |
| Bacteria II | SD-Bact-1522 LD-Bact-132R | TGCGGCTGGATCCCCTC CTTCCGGGTTTCCCCAT TCGG | 5'-6FAM | 2.5 | 4 | Ranjard et al 2001 | 3 4 |

Soil samples were amplified in a 20 µl reaction mix containing 2 µl (10-40 ng) total extracted DNA, 4 pmol each primer, 2 µg BSA, 2.5-3.5 mM MgCl2 depending on primer pair (Table 5), 0.2 mM dNTPs, and 0.825 units Taq F1 DNA polymerase with 1×reaction buffer (Fisher Biotech, Wembley, Western Australia). The amplification was carried out in an Axygen Maxygene thermal cycler, with a program of: 5 minutes at 94° C.; 30 cycles of 30 seconds at 94° C., 30 seconds at 55° C., 1 minute at 72° C.; followed by a final 10 minutes at 72° C.

After amplification, reactions of different primer pairs for the same DNA sample were pooled into the post-PCR multiplex groups indicated in Table 6, and unincorporated primers were removed using RapidTips2 (Diffinity Genomics, New York, USA) as per manufacturer's instructions.

Fragment quantification was carried out on an AB 3730xl at the Australian Genome Research Facility (Perth, Western Australia) using 0.21 µl LIZ1200 size standard and 1.2 µl each multiplex pool in 10 µl HiDi formamide (Life Technologies, Carlsbad, USA).

Peaks corresponding to different ITS length variants within each amplified sample were detected in the resultant fragment datasets using Peak Scanner (version 2.0; Life Technologies, Carlsbad, USA), with minimum peak height set to 50 fluorescence units. Data sets were manually trimmed to 50-1200 base pairs, and binned into 2 base pair bin widths using Interactive Binner (Ramette 2009) running under R 3.0.1 (R Core Team 2013) to generate OTU data for each primer pair.

Differences in total OTU counts from each primer pair were tested across treatments using poisson-distributed generalized linear models in R 3.0.1 (R Core Team 2013). We tested for shifts in the community composition of each primer pair across treatments by comparing the presence and absence of different OTUs, using the Jaccard index, and analysing the data using multivariate statistics (adonis in Vegan v2.07, Oksanen et al 2013, running under R 3.0.1, R Core Team 2013). Plots of community composition were visualised by optimized multidimensional scaling ordinations (metaMDS in MASS v7.3, Venables and Ripley 2002, running under R 3.0.1, R Core Team 2013).

TABLE 7

Results of ARISA assays on the Buntine wheat factorial experiment, with nine plots treated with urea nitrogen fertilizer or Bioprime 20/50 ferment.

| | OTU Count Analysis | | | | | | OTU Composition Analysis | | | |
|---|---|---|---|---|---|---|---|---|---|---|
| | Nitrogen | | | 20/50 Ferment | | | Nitrogen | | 20/50 Ferment | |
| Group | F | P | Effect | F | P | Effect | F | P | F | P |
| Bacteria I | 5.01 | 0.082 | | 7.40 | 0.025* | Suppression | 0.92 | 0.634 | 0.80 | 0.839 |
| Firmicutes | 11.15 | 0.004** | Stimulation | 3.07 | 0.216 | | 1.05 | 0.413 | 1.29 | 0.048* |
| Actinobacteria | 13.40 | 0.001** | Suppression | 61.70 | 0.000*** | Stimulation | 1.14 | 0.195 | 1.79 | 0.002** |
| Bacteria III | 17.28 | 0.000*** | Stimulation | 10.04 | 0.007** | Suppression | 1.37 | 0.038* | 1.10 | 0.273 |
| Gamma Proteobacteria | 2.70 | 0.260 | | 15.90 | 0.000*** | Suppression | 1.24 | 0.028* | 0.99 | 0.519 |
| Archaea | 4.21 | 0.122 | | 39.84 | 0.000*** | Stimulation | 1.00 | 0.504 | 1.01 | 0.441 |
| Dikaryotic Fungi | 4.51 | 0.105 | | 3.39 | 0.184 | | 1.09 | 0.272 | 1.45 | 0.012* |
| Bacteriodetes | 14.68 | 0.001*** | Suppression | 0.27 | 0.874 | | 1.05 | 0.287 | 1.07 | 0.241 |
| Bacteria II | 13.73 | 0.001** | Suppression | 10.34 | 0.006** | Suppression | 1.09 | 0.389 | 2.08 | 0.012* |

Table 7 reports the results of analysing OTU counts per primer using generalized linear models, and of analysing OTU composition by the presence/absence Jaccard index using multivariate statistics. In each case, the table reports the F statistic, the probability value (P) and indicates significance (*-$p<0.05$, -$p<0.01$, *-$p<0.001$). For the OTU count analysis, the direction of the treatment effect (compared to no addition of treatment) is also indicated where the treatment was significant.

Figure 9:
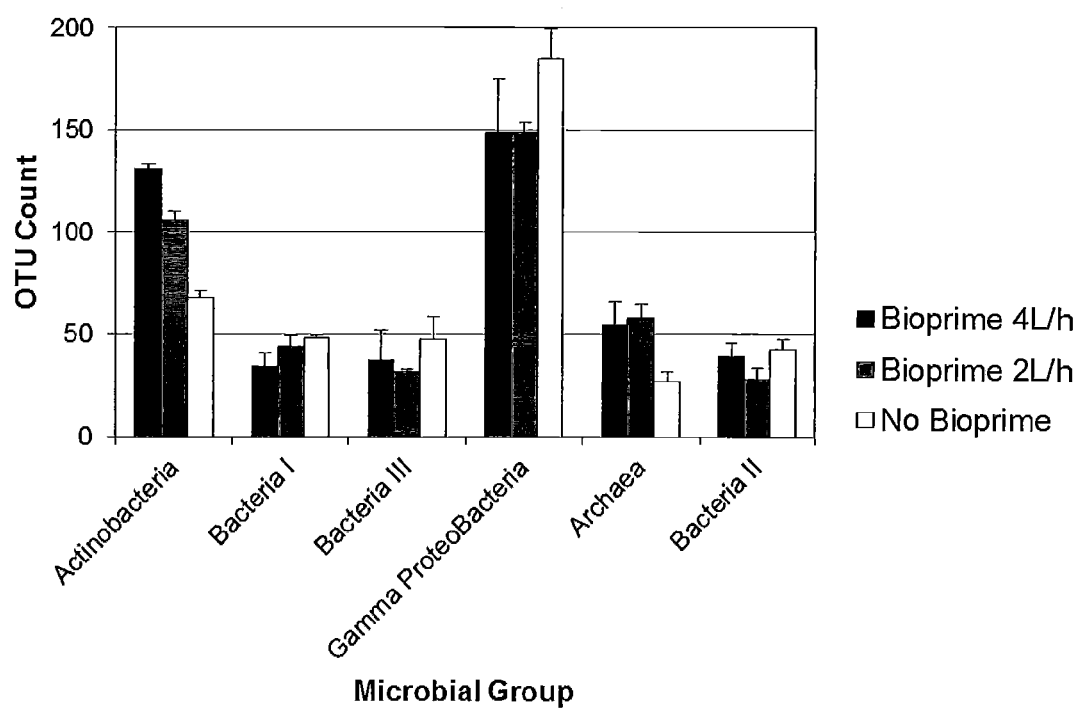
FIG. 9 shows a plot of the effects of 20/50 ferment on the operational taxonomic unit (OTU) count of microbial groups as assayed by ARISA. The plot shows only those groups that were significantly changed by treatment. The bars show the average count per treatment+1 standard error.
Figure 10:
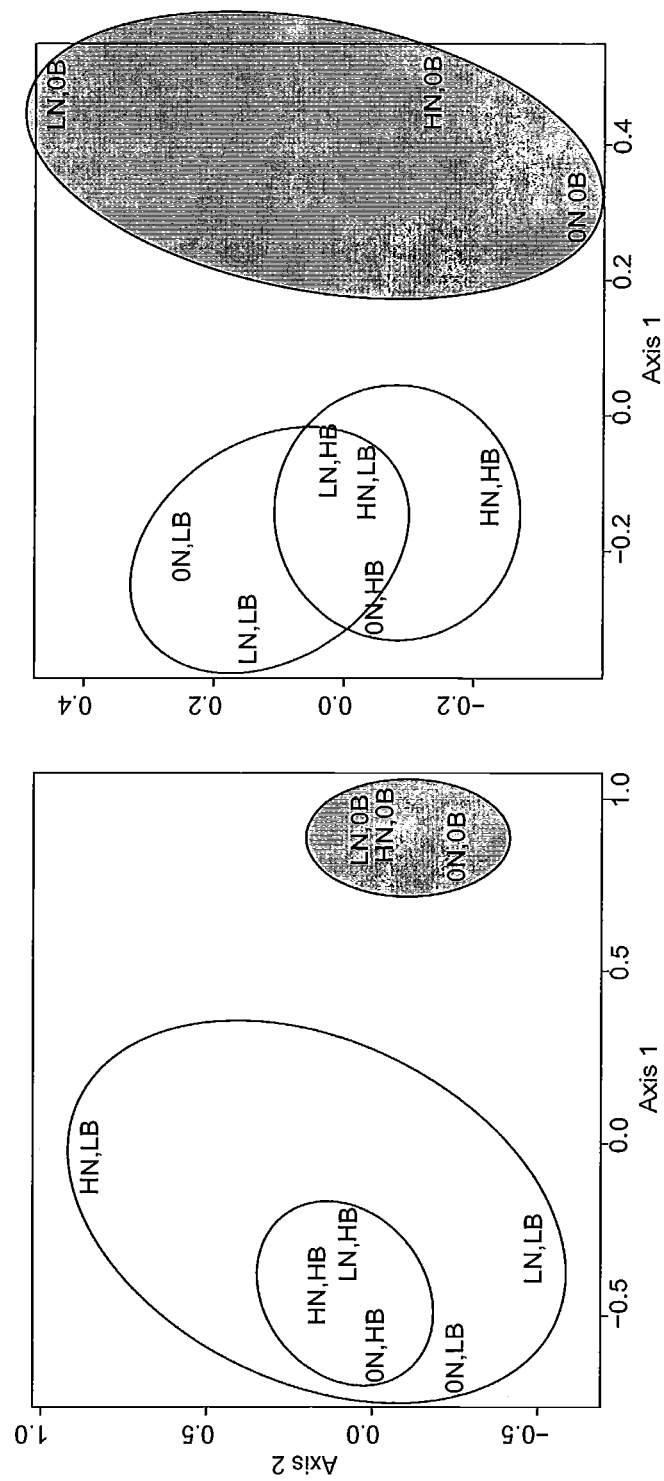
FIG. 10 shows the effects of 20/50 ferment on the OTU community composition of (a) Actinobacteria and (b) Dikaryotic fungi. The plots are optimized multidimensional scaling ordinations of OTUs (presence/absence data) for each group plotted onto the two axes that explain the most variance in the ordination of the datasets. Letters indicate the locations of the nine plots on the ordination axes and their treatments received for nitrogen (none—0N, low—LN, high—HN) and 20/50 ferment (none—0B, low—LB, high—HB). Overlain ellipses (fitted by eye) delineate 20/50 fermented sugar treatment groups, with the shaded ellipse delineating the no 20/50 ferment group.

The ARISA assay results showed that both nitrogen and 20/50 ferment treatments independently changed both the OTU counts of some microbial groups, and also the composition of OTUs present or absent within some microbial groups (Table 7, FIGS. 9 and 10). Significant suppressive and stimulatory effects of both nitrogen and 20/50 on ARISA OTU counts were found (Table 7, FIG. 9). For Actinobacteria and Bacteria III where both nitrogen and 20/50 ferment had significant effects on ARISA OTU counts, treatment effects acted in opposite directions (Table 7, FIG. 9). For example, nitrogen treatment suppressed the ARISA OTU count for Actinobacteria, while 20/50 ferment concomitantly stimulated the ARISA OTU count for Actinobacteria (Table 7, FIG. 9). Actinobacteria are a large and common group of soil bacteria. They are aerobes and functionally they oxidate complex plant organic compounds. Because many species secrete fungal antibiotics into the soil, they are believed to inhibit the growth of plant fungal pathogens (Goodfellow and Williams 1983). 20/50 ferment treatment significantly shifted the OTU community composition of both Actinobacteria and Dikaryotic fungi in the ARISA assay (Table 7, FIG. 10).

Example 4

Onion Growth

Trial beds were Bassendean sands in Forrestdale, irrigated by bore water using butterfly sprinklers on 7 m centres. Beds were prepared by rotary hoeing and formed to be 1 m wide and 10 m long. Two parallel beds were formed, then broken into 1 m sections marked with stakes.

The 20 m² of beds had pre-plant fertiliser of superphosphate (1 Kg), magnesium sulphate (300 g) manganese sulphate (50 g) boric acid (30 g) copper sulphate (10 g) iron sulphate (10 g) zing sulphate (10 g) and sodium molybdate (2 g). Fertilisers were blended in a bucket before being broadcasted evenly over the beds.

Onion seeds ("Bianca" variety) were hand sown in three rows 200 mm apart in each bed. Seed was placed approximately 40 mm apart.

Once seeds were sown, beds were randomly assigned a treatment. There were three treatments, being the application of fermentation product 20/50 using rates of 10 L per hectare or 20 L per hectare or untreated controls. Sufficient volume of the product was dissolved in tap water and applied evenly using a watering can. There were six replicates of each product treatment and eight control replicates. Four week after onions had germinated, the same treatments were reapplied.

Six weeks after beds were sown, one seedling from each 1 m² treatment block was carefully recovered so as to keep soil adhering to roots. Samples from each treatment were aggregated together, and soil had DNA extracted. The DNA was subjected to ARISA analysis.

Twenty two weeks after seeds were sown, onions showed signs of maturation, so irrigation was turned off. Onions were harvested 2 weeks later by pulling from soil and laying on plastic sheet to dry. Dried leaves were removed and bulbs were counted and weighed.

TABLE 8

| | ARISA Results | | |
|---|---|---|---|
| Taxa Present | Control | 20/50 at 10 L/ha | 20/50 at 20 L/ha |
| BacI | 194 | 196 | 182 |
| Gamma Proteobacteria | 14 | 38 | 62 |
| Firmicutes | 51 | 61 | 69 |
| Archea | 62 | 102 | 124 |

TABLE 8-continued

| | ARISA Results | | |
|---|---|---|---|
| Taxa Present | Control | 20/50 at 10 L/ha | 20/50 at 20 L/ha |
| Actinobacteria | 109 | 51 | 10 |
| Dikarya | 11 | 46 | 64 |

Results from the ARISA analysis show that onion rhizosphere soil had significantly different microbial populations in some groups when 20/50 was applied. Gamma proteobacteria increased as more product was applied, as did Archea and Dikarya, whereas Actinobacteria declined.

TABLE 9

| | Harvest Results | | |
|---|---|---|---|
| | Control | 20/50 at 10 L/ha | 20/50 at 20 L/ha |
| Harvested weight/bed (var) | 2.41 (0.91) | 3.12 (0.6) | 3.61 (0.09) |
| Marketable weight (var) | 1.81 (0.41) | 3.02 (0.21) | 3.51 (0.06) |
| % difference | | +67% | +94% |

The treatment of beds with 20/50 immediately after sowing, and again 4 weeks later promoted a significant increase in harvested weight, and a reduction of variability between bulbs. In the untreated controls, 25% of the harvest was unmarketable because of small sized or misshaped bulbs, whereas losses in the treated groups were much lower at 3%. Overall, 20/50 ferment produced at 67% increase in marketable onions when applied at 10 L/ha, and a 94% increase when applied at 20 L/ha.

These increases were associated with a pronounced increase in root dikarya, and gamma proteobacteria, and a decrease in root actinobacteria.

Example 5

Native Plant Regrowth and Rehabilitation

Areas designated for native plant regrowth were located surrounding Lake Gnangara, north of Perth, applied in November 2012 The areas were administered 20/50 ferment at a rate of 5 ml per plant, dissolved in 2 L of water The compositions of leaf tissue from various plants sampled from the native plant regrowth areas were analysed 4 months after the application of 20/50 ferment using the technique described in Example 2. The results are provided in Tables 10 to 12

TABLE 10

| | Leaf Tissue Results - *Banksia* | | | |
|---|---|---|---|---|
| Element | *Banksia* 20/50 1 | *Banksia* 20/50 2 | *Banksia* control 1 | *Banksia* control 2 |
| Total Nitrogen (%) | 0.97 | 0.82 | 1.14 | 0.40 |
| Total Phosphorous (%) | 0.04 | 0.03 | 0.10 | 0.05 |
| Potassium (%) | 0.70 | 0.58 | 0.96 | 0.38 |
| Calcium (%) | 0.18 | 0.27 | 0.29 | 0.28 |
| Magnesium (%) | 0.29 | 0.31 | 0.22 | 0.23 |
| Sodium (%) | 0.26 | 0.26 | 0.38 | 0.31 |
| Iron (mg · kg$^{-1}$) | 172.0 | 145.4 | 116.3 | 118.6 |
| Manganese (mg · kg$^{-1}$) | 208.9 | 46.0 | 56.0 | 82.9 |
| Copper (mg · kg$^{-1}$) | 17.6 | 106.5 | 6.54 | 7.89 |
| Zinc (mg · kg$^{-1}$) | 17.6 | 17.0 | 15.2 | 36.1 |

TABLE 11

Leaf Tissue Results - *Eucalyptus rudis*

| Element | E. rudis 20/50 1 | E. rudis 20/50 2 | E. rudis control 1 | E. rudis control 2 |
|---|---|---|---|---|
| Total Nitrogen (%) | 3.12 | 7.35 | 0.93 | 1.39 |
| Total Phosphorous (%) | 0.16 | 0.16 | 0.06 | 0.08 |
| Potassium (%) | 1.03 | 0.92 | 0.40 | 0.56 |
| Calcium (%) | 0.26 | 0.31 | 0.75 | 0.63 |
| Magnesium (%) | 0.20 | 0.22 | 0.24 | 0.12 |
| Sodium (%) | 0.40 | 0.43 | 0.18 | 0.03 |
| Iron (mg · kg$^{-1}$) | 204.6 | 290.6 | 84.2 | 111.6 |
| Manganese (mg · kg$^{-1}$) | 55.5 | 99.5 | 61.2 | 23.7 |
| Copper (mg · kg$^{-1}$) | 15.0 | 29.2 | 7.89 | 17.5 |
| Zinc (mg · kg$^{-1}$) | 45.0 | 49.8 | 16.4 | 23.3 |

TABLE 12

Leaf Tissue Results - *Acacia*

| Element | Acacia 20/50 1 | Acacia 20/50 2 | Acacia control 1 | Acacia control 2 |
|---|---|---|---|---|
| Total Nitrogen (%) | 1.48 | 1.43 | 3.14 | 1.97 |
| Total Phosphorous (%) | 0.13 | 0.06 | 0.09 | 0.09 |
| Potassium (%) | 1.14 | 0.49 | 0.38 | 0.99 |
| Calcium (%) | 0.51 | 0.60 | 0.50 | 0.22 |
| Magnesium (%) | 0.62 | 0.28 | 0.13 | 0.21 |
| Sodium (%) | 0.06 | 0.09 | 0.34 | 0.15 |
| Iron (mg · kg$^{-1}$) | 249.3 | 29.4 | 115.3 | 104.9 |
| Manganese (mg · kg$^{-1}$) | 105.1 | 89.4 | 36.4 | 21.8 |
| Copper (mg · kg$^{-1}$) | 27.7 | 15.6 | 3.44 | 5.52 |
| Zinc (mg · kg$^{-1}$) | 81.6 | 80.5 | 17.7 | 11.5 |

The microbial diversity of soil samples collected from the roots of the three native plants whose leaf tissue was tested above was also tested in accordance with the technique of Example 3.

TABLE 13

Results of ARISA assay

| Sample | Species | Treatment | Actinobacteria | *Archaea* | BacI | BacIII | Dikarya |
|---|---|---|---|---|---|---|---|
| 192 | rudis | 20/50 ferment | 55 | 9 | 93 | 49 | 56 |
| 193 | rudis | 20/50 ferment | 56 | 7 | 86 | 56 | 48 |
| 195 | acacia | 20/50 ferment | 80 | 3 | 80 | 74 | 33 |
| 194 | acacia | 20/50 ferment | 71 | 233 | 90 | 83 | 22 |
| 196 | banksia | 20/50 ferment | 40 | 5 | 96 | 37 | 69 |
| 197 | banksia | 20/50 ferment | 51 | 4 | 82 | 72 | 46 |
| 201 | rudis | Control | 92 | 2 | 181 | 78 | 51 |
| 202 | rudis | Control | 98 | 4 | 159 | 95 | 52 |
| 198 | banksia | Control | 51 | 8 | 127 | 85 | 55 |
| 199 | banksia | Control | 47 | 6 | — | 86 | 31 |
| 200 | acacia | Control | 89 | 3 | 143 | 131 | 50 |
| 240 | acacia | Control | 70 | 176 | 101 | 103 | 21 |
| | Overall | 20/50 ferment | 59.6 | 50.4 | 86.8 | 64.4 | 43.6 |
| | Overall | Control | 72 | 5 | 155.7 | 86 | 47.25 |

The application of 20/50 ferment increased the levels of measured nutrients in the leaf tissue of native plants tested compared to untreated plants, with different impacts on each species. The most consistent increase was the increase in trace element uptake.

The 20/50 ferment also altered the microbial profile of the rhizosphere.

Figure 11A:
FIGS. 11A and B show the differences in plant growth of areas treated with the 20/50 ferment according to the present invention (A) and untreated areas (B) of native plant regrowth.
Figure 11B:
Figure 12A:
FIGS. 12A and B show the differences in growth of *Eucalyptus rudis* plants treated with the 20/50 ferment according to the present invention (A) and untreated (B).
Figure 12B:
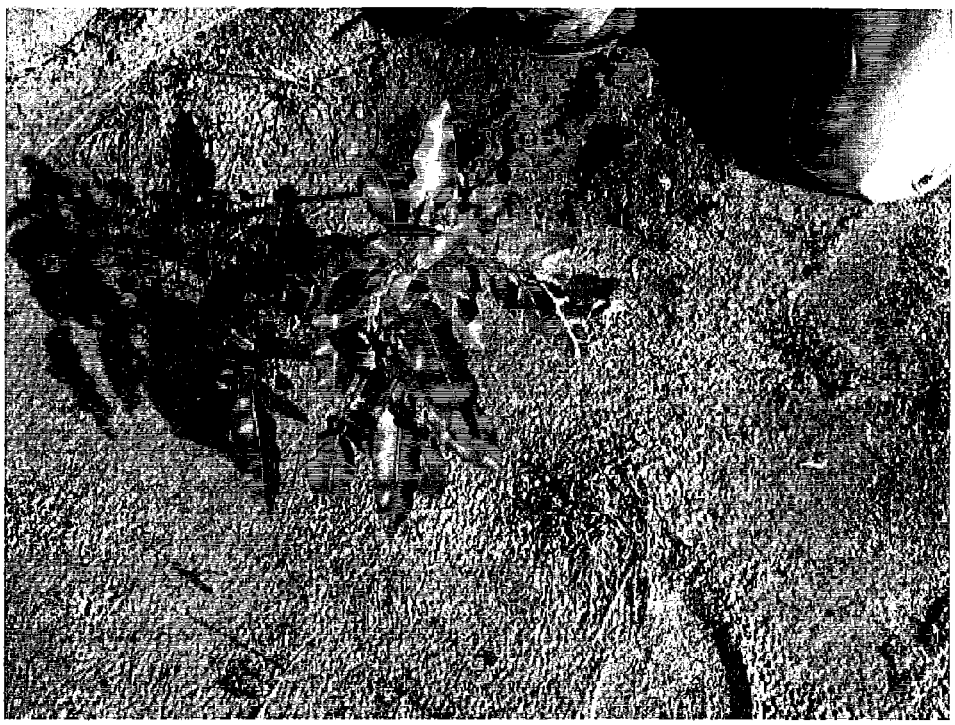
Figure 13A:
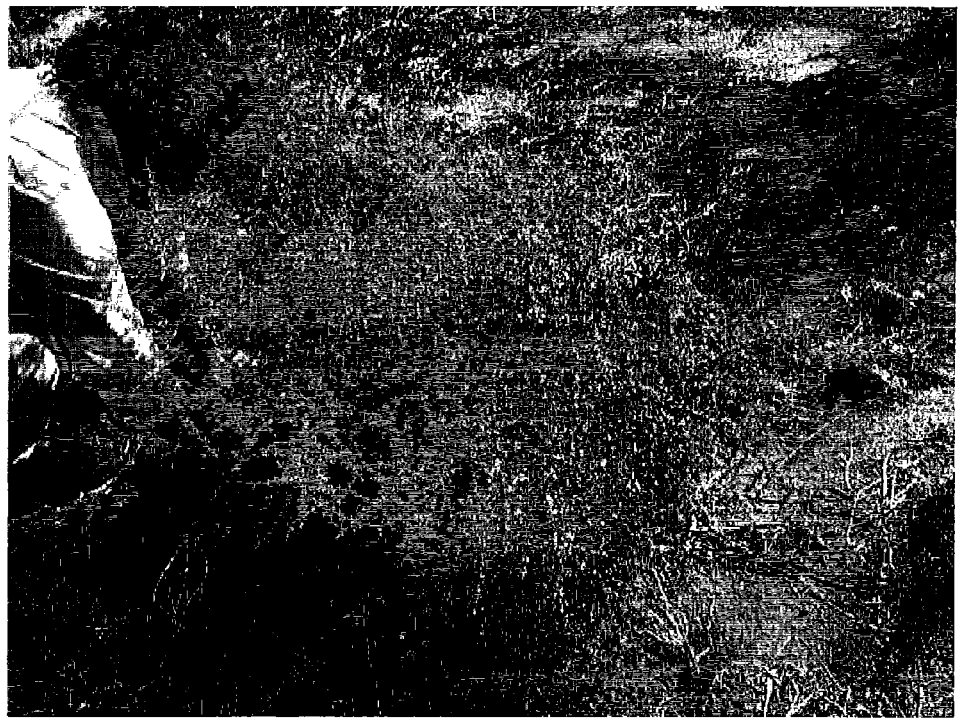
FIGS. 13A and B show the differences in growth of Acacia plants treated with the 20/50 ferment according to the present invention (A) and untreated (B).
Figure 13B:
Figure 14A:
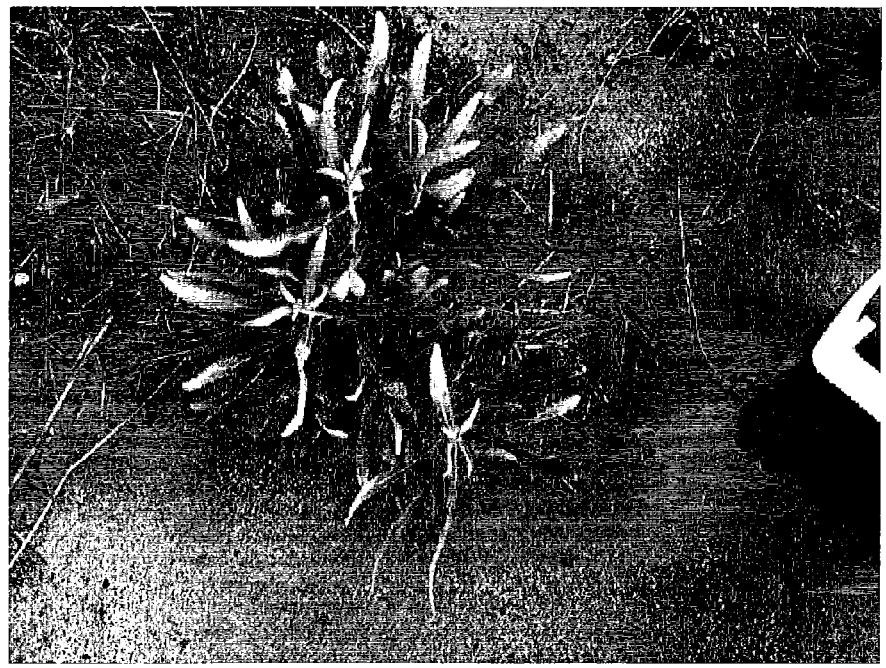
FIGS. 14A and B show the differences in growth of Banksia plants treated with the 20/50 ferment according to the present invention (A) and untreated (B).
Figure 14B:
Figure 15:
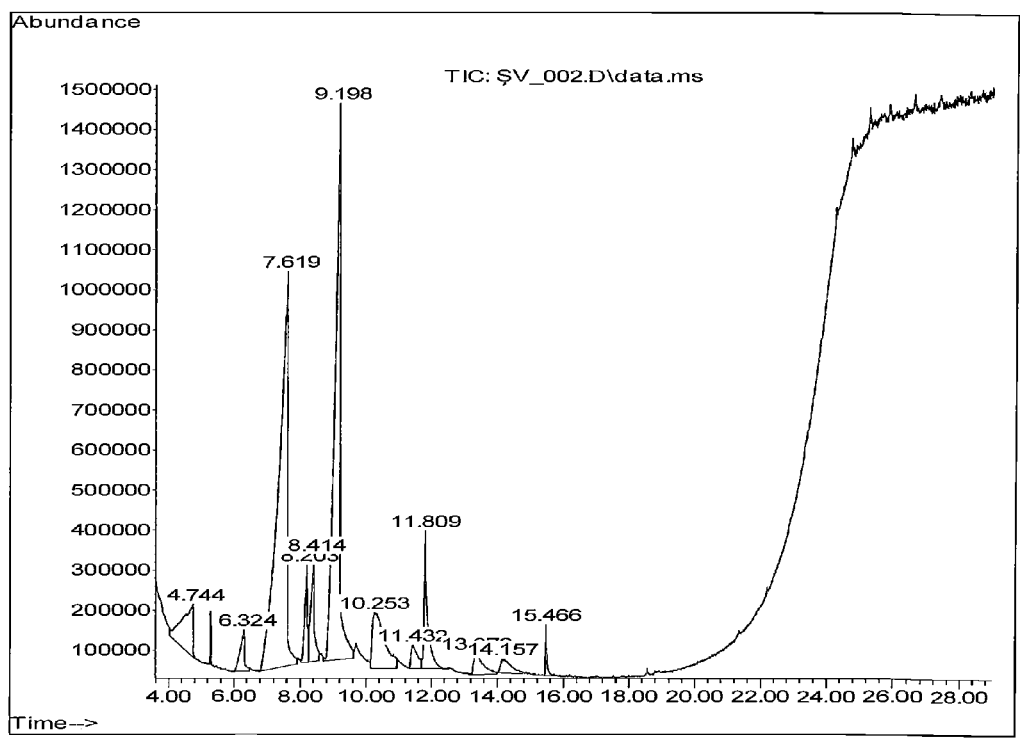
FIG. 15 is a LC/MS/MS plot of peaks produced by Vitazyme.
Figure 16:
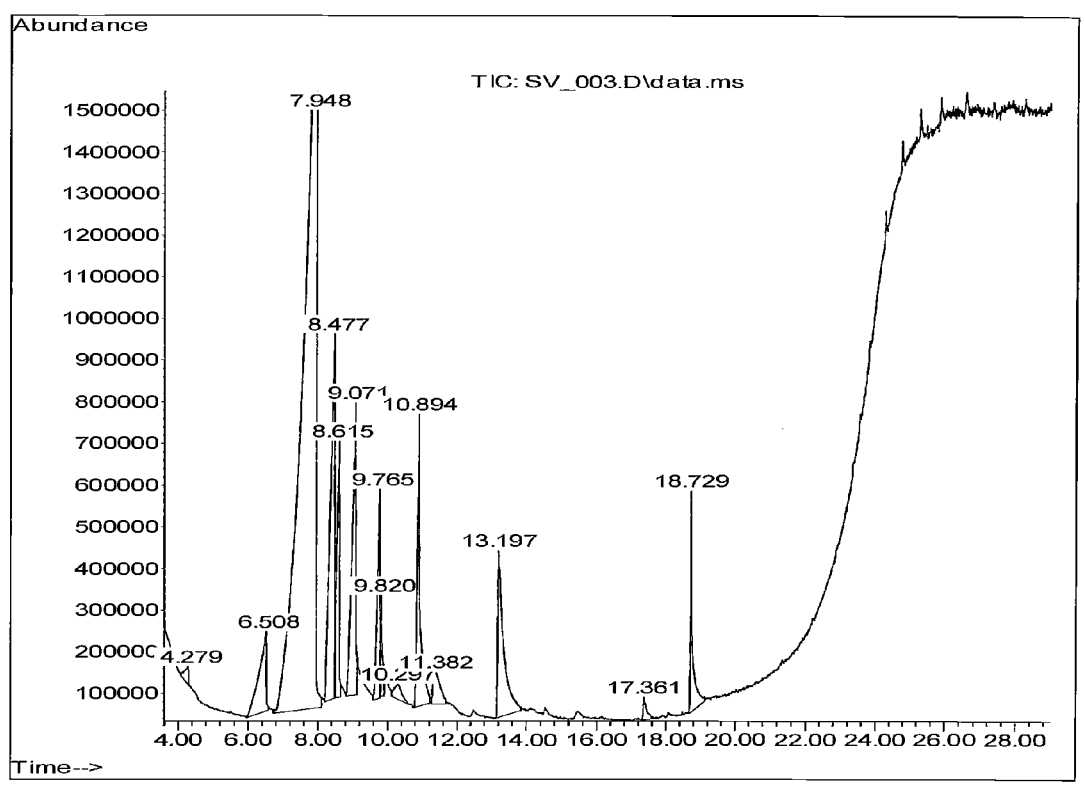
FIG. 16 is a LC/MS/MS plot of peaks produced by TM Ag.
Figure 17:
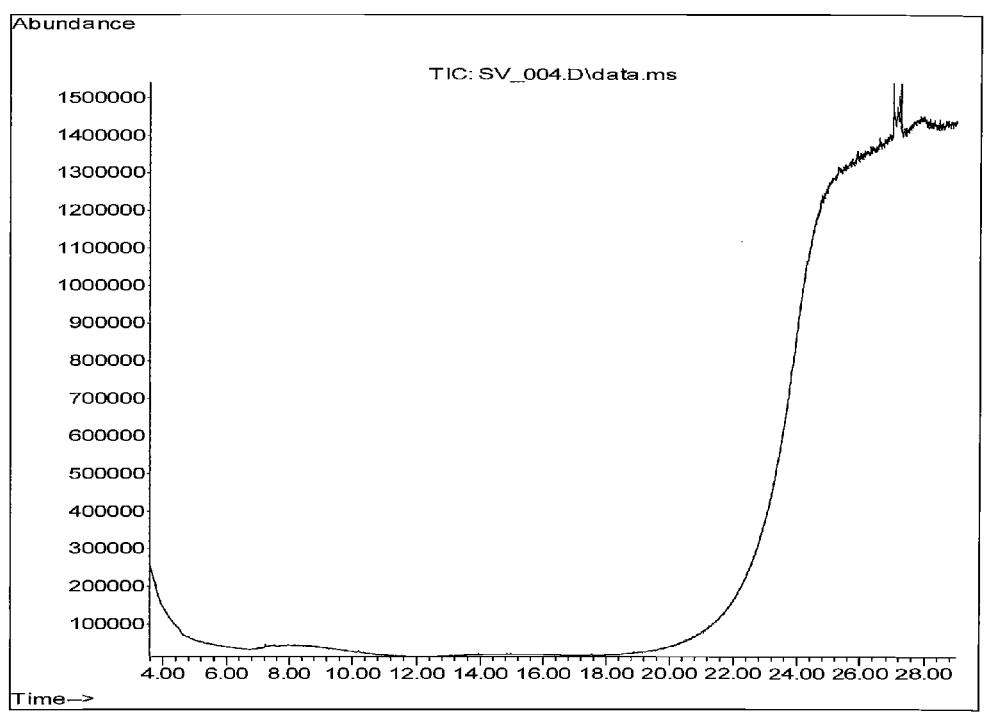
FIG. 17 is a LC/MS/MS plot of peaks produced by expired TM Ag.
Figure 18:
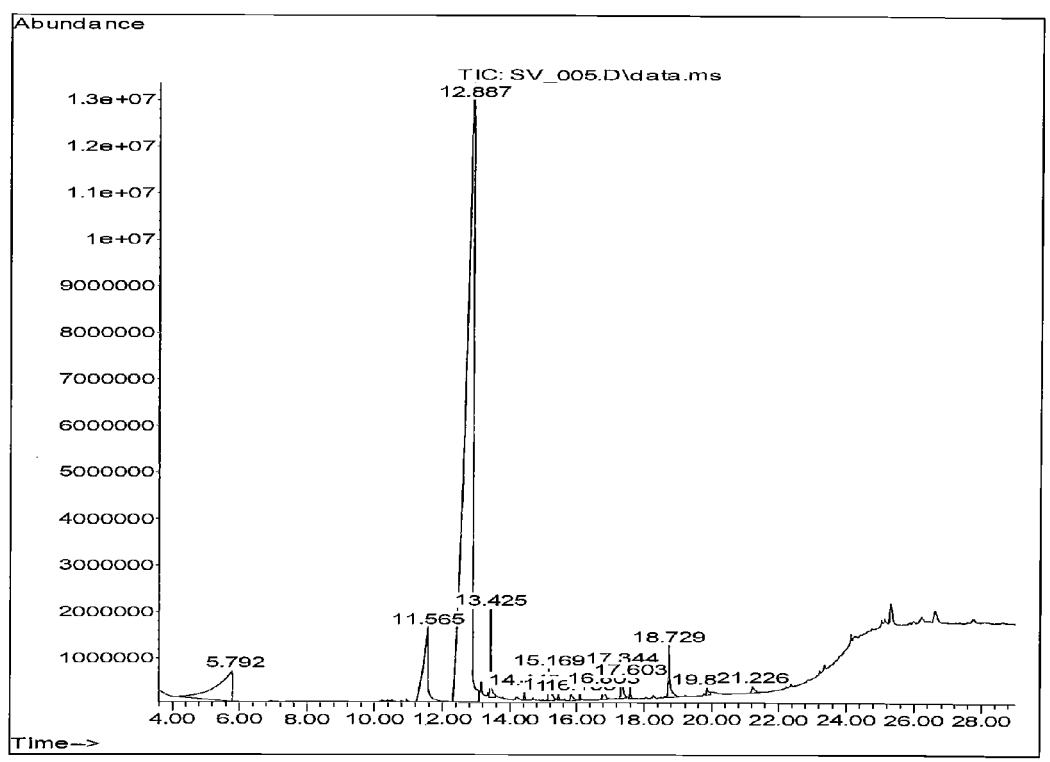
FIG. 18 is a LC/MS/MS plot of peaks produced by Mycorcin.
Figure 19:
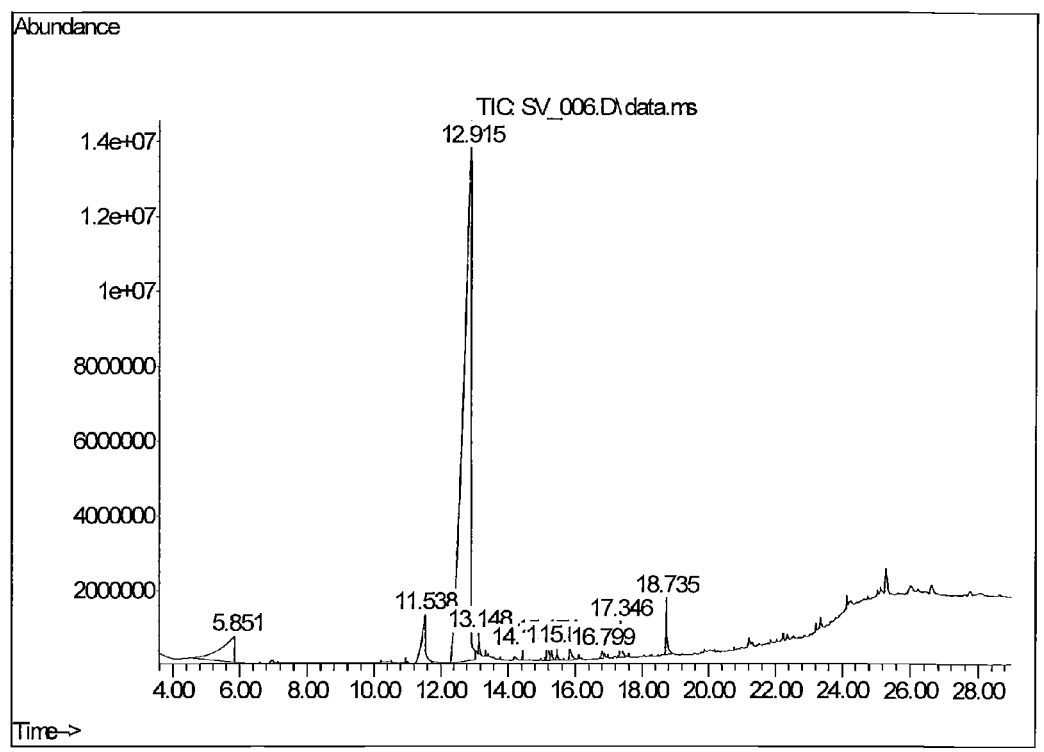
FIG. 19 is a LC/MS/MS plot of peaks produced by Digestor.
Figure 20:
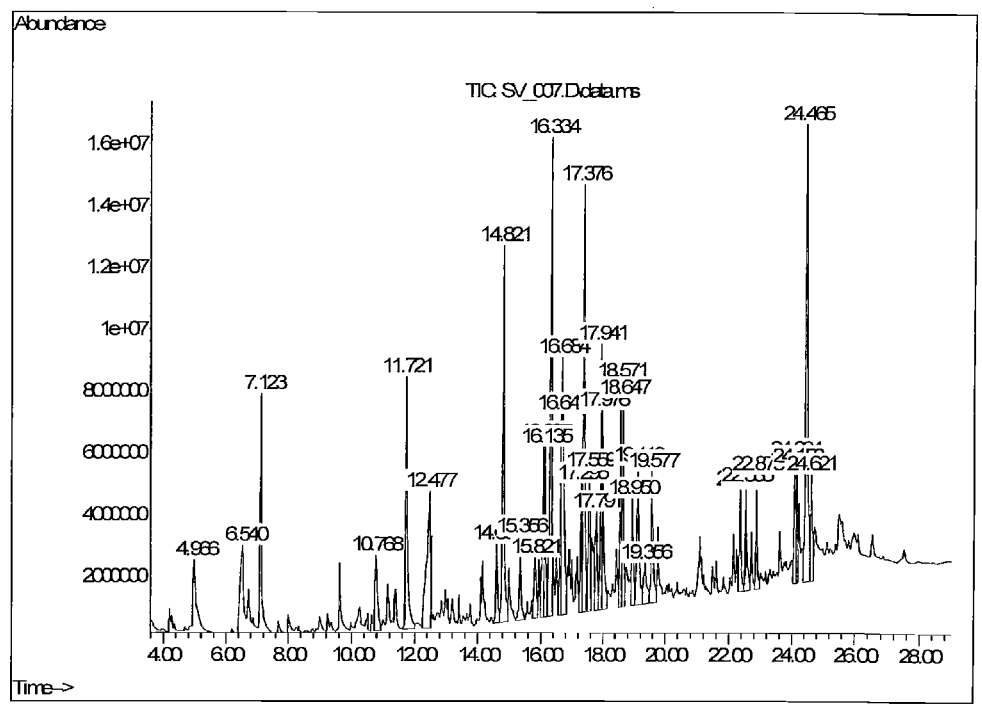
FIG. 20 is a LC/MS/MS plot of peaks produced by Bioprime 20/50 ferment.
Figure 21:
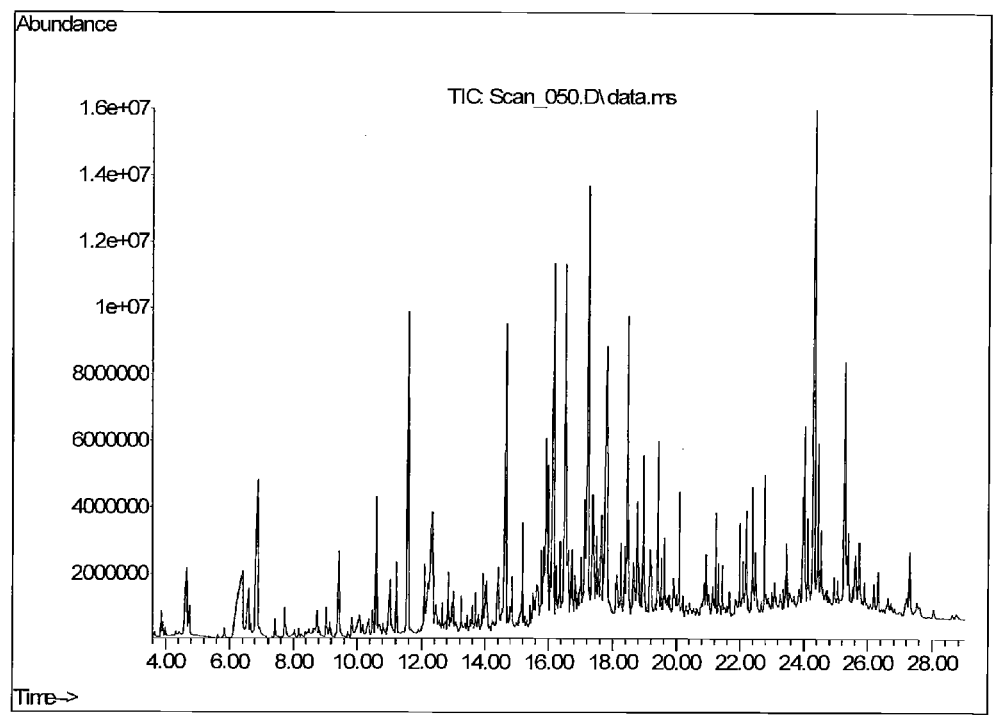
FIG. 21 is a LC/MS/MS plot of peaks produced by Bioprime 20/50 ferment.

Furthermore, application of the ferment greatly promoted plant growth, as shown in FIG. 11A/B to FIG. 14A/B.

Example 6

Fermentation of Cane Sugar

Three reaction vessels were set up with each one containing 814 g of cane sugar (sucrose), 80 g of urea, 40 g of magnesium sulphate, 20 g of monopotassium phosphate and 5 g of "Thrive" brand soluble complete fertiliser. Vessel one had 1.45 L of water added, Vessel 2 had 0.95 L of water added and Vessel 3 had 0.84 L of water added. All vessels then had 1 g of yeast added and the mixture stirred until all contents had dissolved. Each vessel was sealed, and each day over the next 70 days each vessel was opened and the contents stirred vigorously to release carbon dioxide and replenish oxygen before the vessel was again sealed.

Periodically over the 70 day incubation time, a sample was recovered to measure specific gravity, pH and electrical conductivity.

At the completion of 70 days, citric acid and urea were added to 5% w/v of each and dissolved in the ferment.

Example 7

Effect of Fermented Cane Sugar on Crop Growth

The same methodology as described in Example 2 was used at Forrestdale in 2013, using a ferment product manufactured from cane sugar.

A new soil area not previously cultivated was used. No fertiliser was added for the duration of the trial. Soil analysis showed Colwell extractable phosphate at 6.9 mg/kg, organic carbon was 0.41% and pH was 6.5. This is considered a low fertility soil.

Cane sugar ferment was applied at 2 L per hectare at sowing, and/or at 4 L/ha at the two leaf stage (3 weeks after sowing) and/or at tillering (5 weeks after sowing). A total of seven different treatments were applied and compared to no treatment, with 4 replicates for each treatment. Each treatment bed was 1 m².

The wheat variety Mace was sown on 14 Jun. 2013. On 12 November each bed was harvested, grain was cleaned and grain weight determined.

TABLE 14

Results of application of 20/50 ferment on wheat growth

| Treatment Number | Details (application rates in Liters per hectare) | Grain weight (g) Harvested (Mean and Std Error) |
|---|---|---|
| 1 | Control (not ferment applied) | 91.5 (6.3) |
| 2 | 2 L at sowing | 103.8 (4.3) |
| 3 | 4 L at 2 leaf | 126.1 (3.7) |
| 4 | 2 L at sowing, 2 L at 2 leaf | 105.1 (8.3) |
| 5 | 2 L at sowing, 4 L at 2 leaf | 116.1 (7.8) |
| 6 | 2 L at sowing, 4 L at tillering | 116.0 (3.8) |
| 7 | 4 L at 2 leaf, 4 L at tillering | 131.2 (4.8) |
| 8 | 4 L at tillering | 115.1 (13.5) |

The results show that in very low fertility soil, the cane sugar ferment produced a minimum of 13% and a maximum of 43% yield improvement.

Example 8

Analysis of Composition of Various Fermented Products

The composition of various fermented soil additives was determined. Analysis of organic content was carried out by taking a dichloromethane extract and subjecting the extract to LC/MS/MS. The results are presented in Tables 16 to 21 and FIGS. 15 to 21.

TABLE 15

Fermented soil additive products tested

| Sample | Soil Conditioner | Producer | Organic Carbon level (mg/L) |
|---|---|---|---|
| 1 | Vitazyme | VitalEarth Resources, Texas | 3600 |
| 2 | TM Ag | Best Environment Technologies, Alberta | 1700 |
| 3 | TM Ag (expired product) | Best Environment Technologies, Alberta | 1000 |
| 4 | Mycorrcin | BioStart, New Zealand | 34000 |
| 5 | Digestor | BioStart, New Zealand | 31000 |
| 6 | Bioprime (20/50 ferment of the invention) | Bioscience, Perth | 7600 |
| 7 | Bioprime (20/50 ferment of the invention) | Bioscience, Perth | 6300 |

TABLE 16

Composition of Sample 1: Vitazyme

| Peak # | LC/MS ID |
|---|---|
| 1 | Propanoic acid |
| 2 | 2-Methylpropanoic acid |
| 3 | Butanoic acid |
| 4 | 2-Methylbutanoic acid |
| 5 | 3-Methylbutanoic acid |
| 6 | Pentanoic acid |
| 7 | Hexanoic acid |
| 8 | 4-Methylphenol |
| 9 | Cyclohexane carboxylic acid |
| 10 | Benzeneacetic acid |
| 11 | Benzenepropanoic acid |
| 12 | Di-tert-butylphenol |

TABLE 17

Composition of Sample 2: TM Ag

| Peak # | LC/MS ID |
|---|---|
| 1 | Propanoic acid |
| 2 | 2-Methylpropanoic acid |
| 3 | Butanoic acid |
| 4 | 2-Methylbutanoic acid |
| 5 | 3-Methylbutanoic acid |
| 6 | Pentanoic acid |
| 7 | 2-Methylpentanoic acid |
| 8 | 4-Methylpentanoic acid |
| 9 | Hexanoic acid |
| 10 | 2-Methylhexanoic acid |
| 11 | 4-Methylphenol |
| 12 | Benzeneacetic acid |
| 13 | Tetradecanoic acid (Myristic acid) |
| 14 | Hexadecanoic acid (Stearic acid) |

Sample 3, the expired TM Ag product, contained no detectable organic compound peaks.

TABLE 18

Composition of Sample 4: Mycorrcin

| Peak # | LC/MS ID |
|---|---|
| 1 | Propanoic acid |
| 2 | Sorbic acid |
| 3 | Benzenecarboxylic acid |
| 4 | Caprolactam |
| 5 | Tetradecane |
| 6 | unknown alkene |
| 7 | 2,4-Di-tert-butylphenol |
| 8 | Dodecanoic acid |
| 9 | Hexadecane |
| 10 | unknown alkene |
| 11 | Tetradecanoic acid (Myristic acid) |
| 12 | Octadecane |
| 13 | Hexadecanoic acid (Stearic acid) |
| 14 | Oleic acid |
| 15 | Octadecenamide |

TABLE 19

Composition of Sample 5: Digestor

| Peak # | LC/MS ID |
|---|---|
| 1 | 3-Hydroxy-2-butanone |
| 2 | 2,4,5-Trimethyldioxolane |
| 3 | 1,1-Diethoxyethane |
| 4 | 3-Methyl-1-butanol |
| 5 | 2-Methylhexene (?) |
| 6 | 2-Methylpropanoic acid |
| 7 | 2,3-Butanediol |
| 8 | (?) |
| 9 | 2-Hydroxypropanoic acid ethyl ester (?) |
| 10 | 3-Methoxypropanoic acid methyl ester (?) |
| 11 | (?) |
| 12 | unknown branched alkane |
| 13 | Phenylethyl alcohol |
| 14 | 1,3-Di-tert-butylbenzene |
| 15 | unknown branched alkane |
| 16 | Tetradecane |
| 17 | 2,4-Di-tert-butylphenol |
| 18 | Hexadecenoic acid ethyl ester |
| 19 | Hexadecanoic acid ethyl ester |
| 20 | Octadecenoic acid ethyl ester |
| 21 | Octadecanoic acid ethyl ester |

TABLE 20

Composition of Sample 6: Bioprime 20/50 ferment

| Peak # | LC/MS ID |
|---|---|
| 1 | 2-Butanol, 3-methyl- |
| 2 | 2-Butanone, 3-hydroxy- |
| 3 | Propanoic acid, ethyl ester |
| 4 | n-Propyl acetate |
| 5 | 1,3-Dioxolane, 2,4,5-trimethyl- |
| 6 | 3-Buten-1-ol, 3-methyl- |
| 7 | 1-Butanol, 3-methyl- |
| 8 | 1-Butanol, 2-methyl-, (.+/−.)- |
| 9 | 1-Pentanol |
| 10 | 3-Pentanol, 2-methyl- |
| 11 | 2-Buten-1-ol, 3-methyl- |
| 12 | Acetic acid, hydroxy-, ethyl ester |
| 13 | 2,3-Butanediol |
| 14 | 2,3-Butanediol |
| 15 | Propanal, 2-methyl- |
| 16 | Propanoic acid, 2-hydroxy-, ethyl ester |
| 17 | 3,5-Dimethylpyrazole-1-methanol |
| 18 | Urethane |
| 19 | 1-Propanol, 3-ethoxy- |
| 20 | 2-Furanmethanol |
| 21 | 1-Hexanol |
| 22 | 1-Butanol, 3-methyl-, acetate |
| 23 | Butanoic acid, 3-hydroxy-, methyl ester |
| 24 | Hexane, 3-methoxy- |
| 25 | 2-Pentanol, 4-methyl- |
| 26 | Propane, 2-ethoxy- |
| 27 | 2-Heptanol |
| 28 | Diethylene glycol tert-butyl ether methyl ether |
| 29 | Butyrolactone |
| 30 | Pyrimidine, 4,6-dimethyl- |
| 31 | Propanol, methoxy-, acetate |
| 32 | Propanoic acid, 3-methoxy-, methyl ester |
| 33 | 2(3H)-Furanone, dihydro-5-methyl- |
| 34 | 2-Butoxyethyl acetate |
| 35 | 2-Hexene, 4-methyl-, (E)- |
| 36 | 2-Pentanol, propanoate |
| 37 | Phenol |
| 38 | 2-Furancarboxylic acid, ethyl ester |
| 39 | Hexanoic acid |
| 40 | Pyrazine, 2-ethyl-6-methyl- |
| 41 | dl-Mevalonic acid lactone |
| 42 | Heptanoic acid, 2-ethyl- |
| 43 | Heptanoic acid, 2-ethyl- |
| 44 | Hexanoic acid, 2-ethyl-3-hydroxy-, methyl ester |
| 45 | Benzyl Alcohol |
| 46 | 3-Buten-2-ol, 2-methyl- |
| 47 | 2(3H)-Furanone, 5-ethyldihydro- |
| 48 | Ethanone, 1-(1H-pyrrol-2-yl)- |
| 49 | Phenol, 2-methoxy- |
| 50 | Phenylethyl Alcohol |
| 51 | Phenol, 2-ethyl- |
| 52 | Butanedioic acid, diethyl ester |
| 53 | Ethyl hydrogen succinate |
| 54 | Benzenecarboxylic acid |
| 55 | 1,2-Benzenediol |
| 56 | Thiophene, 2,3-dihydro- |
| 57 | Benzofuran, 2,3-dihydro- |
| 58 | Divinyl sulfide |
| 59 | Benzenepropanol |
| 60 | Ethane, 1,1'-selenobis- |
| 61 | Benzeneacetic acid |
| 62 | Benzeneacetic acid |
| 63 | 1,2-Benzenediol, 3-methyl- |
| 64 | Phenol, 4-ethyl-2-methoxy- |
| 65 | Benzenemethanol, 4-methoxy- |
| 66 | Benzoic acid, 2-hydroxy- |
| 67 | Thiodiglycol |
| 68 | 2-Methoxy-4-vinylphenol |
| 69 | Butanoic acid, 2-methyl-, hexyl ester |
| 70 | Benzenepropanoic acid |
| 71 | Phenol, 2,6-dimethoxy- |
| 72 | Eugenol |
| 73 | n-Decanoic acid |
| 74 | 2-Cyclopenten-1-one, 2,3,4,5-tetramethyl- |
| 75 | Ethanone, 1-(2-hydroxy-6-methoxyphenyl)- |
| 76 | 1,4-Benzenediol, 2-methoxy- |

TABLE 20-continued

Composition of Sample 6: Bioprime 20/50 ferment

| Peak # | LC/MS ID |
|---|---|
| 77 | Phenol, 3,4-dimethoxy- |
| 78 | Phenol, 3,4-dimethoxy- |
| 79 | Benzeneethanol, 4-hydroxy- |
| 80 | Ethanone, 1-(2-hydroxyphenyl)- |
| 81 | Phenol, 2-methoxy-4-(1-propenyl)- |
| 82 | Benzeneacetonitrile, 4-hydroxy- |
| 83 | Ethanone, 1-(4-hydroxy-3-methoxyphenyl)- |
| 84 | .delta. Nonalactone |
| 85 | Benzoic acid, 4-hydroxy-3-methoxy-, methyl ester |
| 86 | Ethylparaben |
| 87 | Homovanillyl alcohol |
| 88 | Homovanillyl alcohol |
| 89 | 1'-Acetonaphthone |
| 90 | Phenol, 4-(methoxymethyl)- |
| 91 | Dodecanoic acid |
| 92 | 4-Methyl-2,5-dimethoxybenzaldehyde |
| 93 | 3,5-Heptanedione, 2,2,6,6-tetramethyl- |
| 94 | 2,3,4-Trimethoxyphenol |
| 95 | Ethanone, 1-(4-hydroxy-3-methoxyphenyl)- |
| 96 | Phenol, 2,6-dimethoxy-4-(2-propenyl)- |
| 97 | Phenol, 3,4,5-trimethoxy- |
| 98 | 3-Hydroxy-.beta.-damascone |
| 99 | 1-Phenyl-2-hexanone |
| 100 | Phenol, 4-methyl- |
| 101 | Ethanol, 2-(3-methylphenoxy)- |
| 102 | 4-((1E)-3-Hydroxy-1-propenyl)-2-methoxyphenol |
| 103 | Ethanone, 1-(2,5-dimethoxyphenyl)- |
| 104 | 2H-Pyran-2-carboxylic acid, 5-ethylidene-5,6-dihydro-2,3-dimethyl-6-oxo-, [S-(E)]- |
| 105 | Phenol, 2,6-dimethoxy-4-(2-propenyl)- |
| 106 | 1-Butanone, 1-phenyl- |
| 107 | Phenol, 2-(1,1-dimethylethyl)-5-methyl- |
| 108 | Ethanone, 1-(4-hydroxy-3,5-dimethoxyphenyl)- |
| 109 | Benzeneacetic acid, .alpha.-hydroxy-3-methoxy-, methyl ester |
| 110 | 3,5-Dimethoxy-4-hydroxyphenylacetic acid |
| 111 | 3-(3,4-Dimethoxyphenyl)-propionic acid |
| 112 | o-Isopropylphenetole |
| 113 | 1-Methyl-3,5-diisopropoxybenzene |
| 114 | Benzoic acid, 4-hydroxy-3,5-dimethoxy- |
| 115 | Benzoic acid, 4-hydroxy-3,5-dimethoxy- |
| 116 | Diphenylmethane |
| 117 | 3,4-Dimethoxycinnamic acid |
| 118 | Xanthene-9-carboxylic acid |
| 119 | Pyrrolo[1,2-a]pyrazine-1,4-dione, hexahydro-3-(2-methylpropyl)- |
| 120 | n-Hexadecanoic acid |
| 121 | Benzeneacetic acid, .alpha.-phenyl-, methyl ester |
| 122 | 1-(1-Hydroxybutyl)-2,5-dimethoxybenzene |
| 123 | 3(2H)-Benzofuranone, 4,5-dimethyl- |
| 124 | 2-Propenoic acid, 3-(3,4,5-trimethoxyphenyl)- |
| 125 | Xanthene-9-carboxylic acid |
| 126 | 2-Oxo-4-cyano[1,2,4]oxadiazolo[2,3-a]quinoline |
| 127 | Benzeneacetic acid, 4-hydroxy-3-methoxy-, methyl ester |
| 128 | 9,12-Octadecadienoic acid (Z,Z)- |
| 129 | Furan, 2,5-diphenyl- |
| 130 | Octadecanoic acid |
| 131 | 4-[5-(4-Methoxyphenyl)-2-oxazolyl]pyridine |
| 132 | Hexadecanoic acid, butyl ester |
| 133 | 3-Amino-6-ethyl-4-oxo-3,4-dihydrothieno[2,3-d] pyrimidine-2-carboxylic acid, amide |
| 134 | 3-Heptadecene, (Z)- |
| 135 | Benzyl alcohol, 2-[(4-methoxyphenyl)methylthio]- |
| 136 | Tetrahydrodeoxoargentamin |
| 137 | 4-Hydroxy-2-methoxybenzaldehyde |
| 138 | Benzoic acid, 4-methoxy-, heptyl ester |
| 139 | 9-Octadecenamide, (Z)- |
| 140 | 2-Cyclopentenecarboxylic acid, 5-hydroxy-5-methyl-2-(1-methylethyl)-, methyl ester, trans- |
| 141 | Octadecanoic acid, 2-methylpropyl ester |
| 142 | 3-Methyl-1-oxo-2,3-dihydro-1H-pyrazolo[4,3-c][1,10]phenanthroline |
| 143 | [1,1'-Biphenyl]-4,4'-diol, 3,3'-dimethoxy- |
| 144 | Pentanoic acid, 2-methyl-, methyl ester |
| 145 | 1H-Purine, 8-methyl-6-(methylthio)- |
| 146 | Thiophene, 2-nitro- |
| 147 | Androstan-6-one, (5.alpha.)- |
| 148 | 2-Cyclopentenone, 4-methoxycarbonyl-2,4-dimethyl-3-(3-methyl-7-oxo-1,3-octadienyl)- |
| 149 | 7H-Furo[3,2-g][1]benzopyran-7-one, 4,5,6-trimethoxy- |
| 150 | 4-Methoxyformanilide |
| 151 | Benzene, 1,1',1''-(1-ethanyl-2-ylidene)tris- |

TABLE 20-continued

Composition of Sample 6: Bioprime 20/50 ferment

| Peak # | LC/MS ID |
|---|---|
| 152 | 2',4'-Dihydroxy-3'-methylpropiophenone |
| 153 | 4-Methylcarbazole |
| 154 | Hesperetin |
| 155 | 2-(3,4-Dimethoxyphenyl)-7-hydroxy-4-chromanone |
| 156 | Furo[2,3-H]coumarine, 6-methyl-1-(3-methylphenylamino)- |
| 157 | 12-Ethylsophoramine |
| 158 | 4-(1,3-Dioxoindan-2-ylidenemethyl)quinoline |
| 159 | 2(1H)-Pyridinone, 1-cyclohexyl-3,4,5,6-tetramethyl- |
| 160 | Phenol, 4,4'-methylenebis[2,6-dimethoxy- |
| 161 | 3,4-Dimethoxyphenylacetone |
| 162 | Heptacosane |
| 163 | .alpha.-Amino-3'-hydroxy-4'-methoxyacetophenone |
| 164 | 4-(1,1-Dimethylallyl)-9-methoxy-7H-furo[3,2-g][1]benzopyran-7-one |
| 165 | Methanone, (5-hydroxy-3-benzofuryl)(2,5-dimethoxyphenyl)- |
| 166 | Ethanone, 2-(1H-imidazo[4,5-b]pyridin-2-yl)-1-(4-morpholyl)- |
| 167 | Benzeneacetic acid, 4-hydroxy-3-methoxy-, methyl ester |
| 168 | Ethanone, 2-(1H-imidazo[4,5-b]pyridin-2-yl)-1-(4-morpholyl)- |
| 169 | Benzeneacetic acid, 4-hydroxy-3-methoxy-, methyl ester |
| 170 | Aspidinol |
| 171 | 9,10-Anthracenedione, 1,8-dihydroxy-4,5-dinitro- |
| 172 | Dihydrofuran-2-one, 4-(3,4-dimethoxybenzyl)-3-(4-hydroxy-3-methoxybenzyl)- |
| 173 | 2-Butanone,4-(2,4,6-trimethoxyphenyl) |
| 174 | trans-4-Ethoxy-2',3',4'-trimethoxychalcone |
| 175 | 4H-1-Benzopyran-4-one, 2-(3,4-dimethoxyphenyl)-3,7-dimethoxy- |
| 176 | Benzaldehyde, 4-[[4-(acetyloxy)-3,5-dimethoxyphenyl]methoxy]-3-methoxy- |
| 177 | Benzenepentanoic acid, 3,4-dimethoxy-, methyl ester |
| 178 | 1,4-Butanediol, 2,3-bis[(4-hydroxy-3-methoxyphenyl)methyl]-, [R-(R*,R*)]- |
| 179 | 5.alpha.-Cholestane, 4-methylene- |
| 180 | Stigmastan-6,22-dien, 3,5-dedihydro- |
| 181 | Naphtho[2,3-c]furan-1(3H)-one, 3a,4,9,9a-tetrahydro-6-hydroxy-4-(4-hydroxy-3-methoxyphenyl)-7-methoxy-, [3aR-(3a.alpha.,4.alpha.,9a.beta.)]- |
| 182 | .gamma.-Sitosterol |
| 183 | Cholestane-3,6-dione, (5.alpha.,17.alpha.,20S)- |
| 184 | 7,15-Dimethoxytetradehydroabietic acid, methyl ester |
| 185 | 6-Methyl-5-hepten-2-one oxime, o-[(pentafluorophenyl)methyl]- |
| 186 | 9-Hydroxy-9-fluorenecarboxylic acid |
| 187 | 1,3,5,2,4,6-Trioxatriphosphorinane, 2,4,6-triphenyl-, 2,4,6-trioxide |
| 188 | 1,3-Di(2-benzothiazolyl)-1,3-bis(mercaptomethyl)-urea |
| 189 | 9,10-Anthracenedione, 1,4-bis[(4-methylphenyl)amino]- |
| 190 | 8-Amino-6-methoxy-5-[3,5-bis[trifluoromethyl]phenoxy]quinoline |
| 191 | 9H-Xanthene |

TABLE 21

Composition of Sample 7: Bioprime 20/50 ferment

| Peak # | LC/MS ID |
|---|---|
| 1 | 2-Pentanol |
| 2 | Ethanone, 1-(2,6-dihydroxy-4-methoxyphenyl)- |
| 3 | 1-Butanol, 3-methyl- |
| 4 | Tricosane |
| 5 | Propylene Glycol |
| 6 | 2-Buten-1-ol, 2-methyl- |
| 7 | 2,4-Pentanedione |
| 8 | 2,3-Butanediol |
| 9 | 2,3-Butanediol |
| 10 | Propanal, 2-methyl- |
| 11 | Propanoic acid, 2-hydroxy-, ethyl ester |
| 12 | 2-Pentanone, 4-hydroxy-4-methyl- |
| 13 | Hexanoic acid |
| 14 | 2-Furanmethanol |
| 15 | 1,3-Propanediol |
| 16 | 1-Pentanol, 2-methyl-, acetate |
| 17 | (S)-2-Hydroxypropanoic acid |
| 18 | (S)-2-Hydroxypropanoic acid |
| 19 | 2(3H)-Furanone, dihydro-5-methyl- |
| 20 | Acetic acid, butyl ester |
| 21 | Phenol |
| 22 | Hexanoic acid |
| 23 | 6,8-Dioxabicyclo[3.2.1]octane |
| 24 | Heptanoic acid, 2-ethyl- |
| 25 | 1,2-Cyclopentanedione, 3-methyl- |

TABLE 21-continued

Composition of Sample 7: Bioprime 20/50 ferment

| Peak # | LC/MS ID |
|---|---|
| 26 | Benzyl Alcohol |
| 27 | Butanoic acid, 2-hydroxy-3-methyl- |
| 28 | 5H-1,4-Dioxepin, 2,3-dihydro-7-methyl- |
| 29 | Ethanone, 1-(1H-pyrrol-2-yl)- |
| 30 | Phenol, 4-methyl- |
| 31 | Heptanamide, 4-ethyl-5-methyl- |
| 32 | 2,4(1H,3H)-Pyrimidinedione, 5-hydroxy- |
| 33 | Propanoic acid, 3-(methylthio)- |
| 34 | 1,2,3-Propanetriol, 1-acetate |
| 35 | 2,3-Butanedione, monooxime |
| 36 | Phenylethyl Alcohol |
| 37 | Thiourea |
| 38 | Thiourea |
| 39 | 4H-Pyran-4-one, 2,3-dihydro-3,5-dihydroxy-6-methyl- |
| 40 | Benzenecarboxylic acid |
| 41 | Benzenecarboxylic acid |
| 42 | 1,2-Benzenediol |
| 43 | Thiophene, 2,3-dihydro- |
| 44 | Benzofuran, 2,3-dihydro- |
| 45 | Thiophene, 2,3-dihydro- |
| 46 | Benzenepropanol |
| 47 | Benzeneacetic acid |
| 48 | Pyrimidine, 2,4-dimethyl- |
| 49 | Benzoic acid, 2-hydroxy- |
| 50 | 2-Methoxy-4-vinylphenol |
| 51 | Benzenepropanoic acid |
| 52 | Phenol, 2,6-dimethoxy- |
| 53 | Eugenol |
| 54 | 1,4-Benzenediol, 2-methoxy- |
| 55 | Phenol, 3,4-dimethoxy- |
| 56 | Benzeneethanol, 4-hydroxy- |
| 57 | Ethanone, 1-(2-hydroxyphenyl)- |
| 58 | 4,5,5-Trimethyl-spiro[1,2]pentan-3-imidazoline-3-oxide |
| 59 | Phenol, 2-methoxy-4-(1-propenyl)-, (Z)- |
| 60 | Benzeneacetonitrile, 4-hydroxy- |
| 61 | Ethanone, 1-(3-hydroxy-4-methoxyphenyl)- |
| 62 | Benzoic acid, 4-hydroxy- |
| 63 | Benzoic acid, 4-hydroxy-3-methoxy-, methyl ester |
| 64 | Benzeneacetic acid, 4-hydroxy-3-methoxy- |
| 65 | 2,4,6(1H,3H,5H)-Pyrimidinetrione, 5,5-diethyl-1-methyl- |
| 66 | 4-(2-Methoxyethyl)phenol |
| 67 | 3-Hydroxy-4-methoxybenzoic acid |
| 68 | 2,3,4-Trimethoxyphenol |
| 69 | Ethanone, 1-(4-hydroxy-3-methoxyphenyl)- |
| 70 | Phenol, 3,4,5-trimethoxy- |
| 71 | 3-Hydroxy-.beta.-damascone |
| 72 | Benzenepropanoic acid, 4-hydroxy- |
| 73 | Benzenepropanoic acid, 4-hydroxy- |
| 74 | 2H-Pyran-2-carboxylic acid, 5-ethylidene-5,6-dihydro-2,3-dimethyl-6-oxo-,[S-(E)]- |
| 75 | Benzeneacetic acid, .alpha.-hydroxy-3-methoxy-, methyl ester |
| 76 | 4-((1E)-3-Hydroxy-1-propenyl)-2-methoxyphenol |
| 77 | Tetradecanoic acid |
| 78 | 3-(3,4-Dimethoxyphenyl)-propionic acid |
| 79 | Benzoic acid, 4-hydroxy-3,5-dimethoxy- |
| 80 | 1-Propanone, 3-hydroxy-1-(4-hydroxy-3-methoxyphenyl)- |
| 81 | 3,5-Dimethoxybenzamide |
| 82 | 3-Hydroxy-4-methoxycinnamic acid |
| 83 | 3,5-Dimethoxy-4-hydroxyphenylacetic acid |
| 84 | 3,5-Dimethoxy-4-hydroxyphenylacetic acid |
| 85 | 3-(3,4,5-Trimethoxyphenyl)propionic acid |
| 86 | Xanthene-9-carboxylic acid |
| 87 | Pyrrolo[1,2-a]pyrazine-1,4-dione, hexahydro-3-(2-methylpropyl)- |
| 88 | n-Hexadecanoic acid |
| 89 | Benzeneacetic acid, .alpha.-phenyl-, methyl ester |
| 90 | Hexadecanoic acid, ethyl ester |
| 91 | 1-(1-Hydroxybutyl)-2,5-dimethoxybenzene |
| 92 | 8-Methoxy-[1,2,4]triazolo[4,3-a]pyridine-3-thiol |
| 93 | 1(2H)-Naphthalenone, 3,4-dihydro-5-methoxy-8-methyl- |
| 94 | Xanthene-9-carboxylic acid |
| 95 | .beta.-(4-Hydroxy-3-methoxyphenyl)propionic acid |
| 96 | 3,5-Dimethoxy-4-hydroxycinnamic acid |
| 97 | 9,12-Octadecadienoic acid (Z,Z)- |
| 98 | Oleic Acid |
| 99 | 9,12-Octadecadienoic acid, ethyl ester |
| 100 | Ethyl Oleate |
| 101 | Benzeneethanol, 2-(phenylmethoxy)- |

TABLE 21-continued

Composition of Sample 7: Bioprime 20/50 ferment

| Peak # | LC/MS ID |
|---|---|
| 102 | Hexadecanoic acid, butyl ester |
| 103 | Octadecanoic acid, ethyl ester |
| 104 | 5-Octadecene, (E)- |
| 105 | (3S,4R,5R,6R)-4,5-Bis(hydroxymethyl)-3,6-dimethylcyclohexene |
| 106 | 2-Amino-3,5,7,8-tetrahydro-4,6-pteridinedione |
| 107 | (E)-9-Octadecenoic acid ethyl ester |
| 108 | Furan-2-carboxylic acid, 4-diethylaminomethyl-5-ethyl- |
| 109 | Flopropione |
| 110 | Benzoic acid, 3-methoxy-, heptyl ester |
| 111 | 4-n-Heptylbiphenyl |
| 112 | Benzenamine, N-phenyl- |
| 113 | Octadecanoic acid, butyl ester |
| 114 | Ethanone, 1-(2,6-dihydroxy-4-methoxyphenyl)- |
| 115 | 4-Ethylbiphenyl |
| 116 | Ethamivan |
| 117 | 7-(3,4-Methylenedioxy)-tetrahydrobenzofuranone |
| 118 | Pentacosane |
| 119 | Phenol, 3,4,5-trimethoxy- |
| 120 | 3-Lauramidobenzoic acid |
| 121 | Squalene |
| 122 | Pentacosane |
| 123 | (−)-Nortrachelogenin |
| 124 | 6H-[1,3]Dioxolo[5,6]benzofuro[3,2-c][1]benzopyran,6a, 12a-dihydro-3,4-dimethoxy-, (6aR-cis)- |
| 125 | Benzeneacetic acid, 4-hydroxy-3-methoxy-, methyl ester |
| 126 | Hexadecane |
| 127 | 2-Hydroxy-3,4-dimethoxy-alpha-(p-methoxyphenyl)acetophenone |
| 128 | Tetracosane |
| 129 | 9-Tricosene, (Z)- |
| 130 | trans-4-Ethoxy-3',4',5'-trimethoxychalcone |
| 131 | Tetracosane |
| 132 | Ergost-5-en-3-ol, (3.beta.)- |
| 133 | Stigmasterol |
| 134 | .gamma.-Sitosterol |

The total organic carbon in Samples 1 to 3 is quite low at 3.6 and 1.7%. It appears that Samples 1 to 3 are fermented from sugar substrates at concentrations typical for ethanol production, but under sufficiently aerobic conditions such that acids are formed but few alcohols remain, thus there is virtually no esters. Samples 2 and 3 are brewed more slowly that Sample 1, so the acids produced tend to have higher molecular weights. Samples 2 and 3 are not stabilised, thus over time active organic molecules completely disappear. The majority of the organics (about 80%) in Samples 2 and 3 is butanoic acid. None of Samples 1 to 3 contained signalling molecules apart from organic acids, and they contain nothing like the furanones, alkyl 2-ones, ethanones, plant hormones, esters and complex phenolics of the sugar ferments of the present invention.

Samples 4 and 5 have much higher total organic carbon at 31 and 34%. However the vast majority (about >97%) of this carbon is accounted for by potassium fulvate. Samples 4 and 5 have quite a high NPK content, which is not disclosed on the container. If plants improve when treated, it is most likely because nutrient limitations are overcome. It appears that Samples 4 and 5 have some fermentation products, but the product is supplemented with sorbic acid (not naturally produced) and benzoic acid (natural, but not in these proportions) to stabilise the ferment product. Both benzoic acid and sorbic acid are fungicides. Although Sample 4 (Mycorrcin) alleged on the product label that it contained signalling molecules, our studies showed that neither of Samples 4 or 5 contained signalling molecules apart from organic acids, and they contain nothing like the furanones, alkyl 2-ones, ethanones, plant hormones, esters and complex phenolics of the sugar ferments of the present invention.

Samples 6 and 7 are standard Bioprime (20/50 ferment) mixes, showing high levels of complex organic molecules.

Example 9

Use of Sugar Ferment to Increase Soil Wetting

The ability to increase soil wetting was tested on non-wetting soils growing wheat and oats. The paddocks tested were unproductive for at least the past six years. Bioprime (20/50 ferment) was added at 3 L/H at 3 weeks after sowing (two leaf stage of crop growth). Production increased from near zero yield to 4 tonne/H crops.

ARISA analysis of the soil using the technique discussed in Example 3 showed the microflora had distinctly changed. The change had led to the removal of the non-wetting nature of the soils. It is believed that this is a result of Bioprime application consistently increasing the diversity of Actinobacteria, which are known to metabolise the waxes produced by proteobacteria. Such waxes are produced as a drying-stress response, but by coating soil particles make them non-wetting. The current treatment for non-wetting farm soils is the application of clay. The application of Bioprime 20/50 ferment produced a better reversal of non-wetting than any reported claying experiments.

Example 10

Use of Soil Additive on Grape Crops

The 20/50 ferment was administered to three varieties of table grape vines: Red Globe, Crimson Seedless and Flame Seedless, grown in the Swan Valley in Western Australia.

Two weeks after application, leaves were sampled and analysed using the techniques described in Example 1. Results are present in Table 28.

Figure 22:
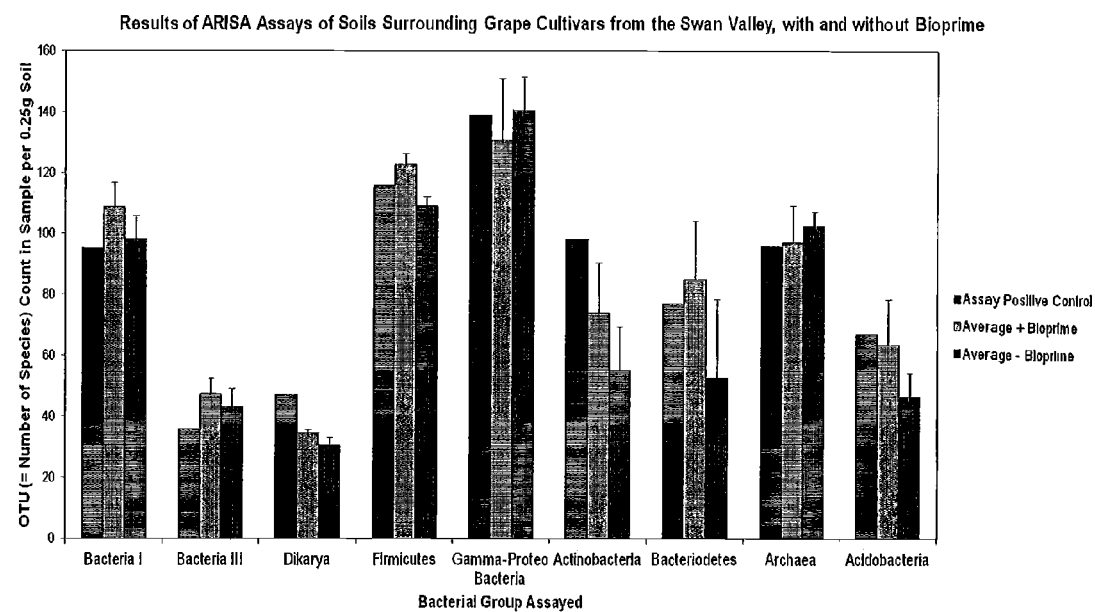
FIG. 22 is a plot of the collated ARISA results of the microbial populations on grape varieties grown with and without the application of Bioprime 20/50 ferment.

Diversity of soil microbial populations was measured using the ARISA technique described in Example 3. Results are present in Table 22, and collated in Table 23 and FIG. 22.

The soil DNA results show a clear increase in overall soil biodiversity with average of 678 OTU's (untreated areas) rising to an average of 763 after 20/50 ferment application.

TABLE 22

Microbial profile analysis of three grape varieties

|  | Positive Control | Crimson+ | Crimson− | Flame+ | Flame− | Red+ | Red− |
|---|---|---|---|---|---|---|---|
| BacI | 95 | 108 | 85 | 95 | 97 | 123 | 112 |
| BacIII | 36 | 45 | 32 | 40 | 51 | 57 | 47 |
| Dicarya | 47 | 33 | 28 | 37 | 28 | 34 | 36 |
| Firmicutes | 116 | 130 | 115 | 121 | 104 | 117 | 108 |
| GPB | 139 | 98 | 154 | 126 | 119 | 168 | 149 |
| Actinobacteria | 98 | 41 | 28 | 91 | 60 | 90 | 77 |
| Bacteriodetes | 77 | 119 | 21 | 52 | 104 | 84 | 33 |
| *Archaea* | 96 | 87 | 93 | 83 | 104 | 121 | 110 |
| Acidobacteria | 67 | 40 | 62 | 60 | 37 | 91 | 41 |
| Total | 771 | 701 | 618 | 705 | 704 | 885 | 713 |

TABLE 23

Combined results of microbial profile analysis

|  | Positive Control | Average + Bioprime | Average − Bioprime | SE+ | SE− |
|---|---|---|---|---|---|
| BacI | 95 | 108.7 | 98.0 | 8.1 | 7.8 |
| BacIII | 36 | 47.3 | 43.3 | 5.0 | 5.8 |
| Dicarya | 47 | 34.7 | 30.7 | 1.2 | 2.7 |
| Firmicutes | 116 | 122.7 | 109.0 | 3.8 | 3.2 |
| GPB | 139 | 130.7 | 140.7 | 20.3 | 10.9 |
| Actinobacteria | 98 | 74.0 | 55.0 | 16.5 | 14.4 |
| Bacteriodetes | 77 | 85.0 | 52.7 | 19.3 | 25.9 |
| Archaea | 96 | 97.0 | 102.3 | 12.1 | 5.0 |
| Acidobacteria | 67 | 63.7 | 46.7 | 14.8 | 7.8 |
| Total | 771 | 763.7 | 678.3 |  |  |

TABLE 24

Leaf nutrient levels in grape varieties grown in presence or absence of 20/50 ferment

| Element | Flame seedless Bioprime | Flame seedless Control | Red Globe Bioprime | Red Globe Control | Crimson Seedless Bioprime | Crimson Seedless Control | Dawn seedless Bioprime | Dawn seedless Control | Ideal Range L/F |
|---|---|---|---|---|---|---|---|---|---|
| Total Nitrogen (%) | 3.75 | 3.95 | 2.97 | 3.17 | 3.24 | 3.65 | 3.54 | 4.19 | 2.2-3.9 |
| Total Phosphorous (%) | 0.63 | 0.57 | 0.49 | 0.48 | 0.52 | 0.38 | 0.42 | 0.44 | 0.15-0.30 |
| Potassium (%) | 1.05 | 1.02 | 1.25 | 1.35 | 0.92 | 1.04 | 1.59 | 1.28 | 0.8-1.6 |
| Calcium (%) | 1.58 | 1.03 | 0.52 | 0.56 | 0.92 | 0.70 | 0.67 | 0.67 | 0.8-3.2 |
| Magnesium (%) | 0.33 | 0.30 | 0.31 | 0.34 | 0.18 | 0.19 | 0.33 | 0.39 | 0.3-0.6 |
| Sodium (%) | 0.07 | 0.05 | 0.05 | 0.06 | 0.06 | 0.06 | 0.10 | 0.07 | <0.2 |
| Iron (ppm) | 66.5 | 121.1 | 103.7 | 221.2 | 106.8 | 122.7 | 155.8 | 109.4 | 30-150 |
| Manganese (ppm) | 374.1 | 315.9 | 81.8 | 121.3 | 161.2 | 145.0 | 218.3 | 95.9 | 25-200 |
| Copper (ppm) | 602.8 | 566.6 | 130.6 | 246.0 | 337.0 | 350.8 | 380.5 | 160.4 | 10-300 |
| Zinc (ppm) | 56.9 | 60.6 | 41.6 | 57.3 | 38.7 | 32.0 | 45.2 | 20.9 | 30-60 |

It was found that the application of 20/50 ferment increased the levels of measured nutrients in the leaf tissue of grape varities tested compared to untreated plants, with different impacts on each grape type. The most consistent increase was the increase in trace element uptake.

The 20/50 ferment also altered the microbial profile of the rhizosphere, with a relative reduction in the diversity and dominance of bacteria belonging to the beta proteobacteria, and an increase in the number of dominant taxa belonging to the dikarya.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

The invention claimed is:

1. A soil additive comprising:
a microbial sugar ferment produced under conditions of high metabolic stress, wherein the high metabolic stress is provided by one or more conditions chosen from high ionic strength, high osmotic pressure, anaerobic stress, and oxidative stress;
wherein said ferment contains signalling molecules, wherein the total organic carbon (TOC) in the ferment is 14-52% (w/v) of the original organic carbon of the fermentation mixture, and the signalling molecules comprise between about 1-50% (w/v) of the TOC present in the ferment, and wherein the signalling molecules are selected from one or more of the following groups: microbial quorum sensors and quenchers, biocides and plant elicitors, and
wherein the soil additive further comprises between 4% and 10% (w/v) organic acid added post-fermentation; and
wherein the signalling molecules in the soil additive comprise at least one furanone compound and/or ethanone compound or esters thereof, and at least one phenolic compound and/or eugenol compound or derivative thereof.

2. The soil additive of claim 1, wherein the sugar ferment contains signalling molecules comprising between about 15-40% (w/v) of the organic matter present in the ferment.

3. The soil additive according to claim 1 comprising a molasses ferment wherein said ferment contains signalling molecules comprising between about 20-25% (w/v) of the organic matter present in the ferment.

4. A method for producing a soil additive comprising:
a) fermenting sugar using a microbe under conditions of high metabolic stress to produce a sugar ferment, wherein the high metabolic stress is provided by one or more conditions chosen from high ionic strength, high osmotic pressure, anaerobic stress, and oxidative stress; wherein the conditions of high metabolic stress result in production of high levels of signalling molecules by the microbe, and wherein the signalling molecules are selected from one or more of the following: microbial quorum sensors and quenchers, biocides and plant elicitors and wherein the signalling molecules in the soil additive comprise at least one furanone compound and/or ethanone compound or esters thereof, and at least one phenolic compound and/or eugenol compound or derivative thereof; and
adding between 4% and 10% (w/v) organic acid to the sugar ferment, after the fermenting.

5. The method of claim 4 wherein the sugar ferment produced contains signalling molecules, wherein the total organic carbon (TOC) is 14-52% (w/v) of the original organic carbon of the fermentation mixture, and the signalling molecules comprise between about 1-50% (w/v) of the TOC present in the ferment.

6. The method of claim 4 wherein the high metabolic stress is provided by a combination of high ionic strength and high osmotic pressure and oxidative stress.

7. The method of claim 6 wherein the high ionic strength and high osmotic pressure are produced by reducing the amount of water in the fermentation mixture to between 0.5 x and 4.0 x (v/v) the volume of solids in the fermentation mixture.

8. The method of claim 6 wherein the oxidative stress is produced by reducing the oxygen level to between about 0.1 and 8.5 ppm dissolved $O_2$.

9. The soil additive of claim 1 wherein the organic acid added post-fermentation is citric acid.

10. The soil additive of claim 1 wherein the signalling molecules include campesterol, sigmasterol and sistosterol.

11. A soil additive composition produced by the process according to claim 4.

12. A method for producing a soil additive comprising:
(a) creating a fermentation mixture comprising at least one sugar, water, and a microbe; wherein the microbe is a fungi having a budding single cell phase; and wherein the weight ratio of sugar to water in the fermentation mixture is at least 1:1 and less than 1:2.5;
(b) fermenting the fermentation mixture under conditions of high metabolic stress to the microbe to produce a sugar ferment, wherein the high metabolic stress in is provided by one or more conditions selected from high ionic strength, high osmotic pressure, anaerobic stress, and oxidative stress, such that 14-52% (w/v) of the initial carbon added to the fermentation mixture remains as fermentation product in the sugar ferment, when substantially all of the sugar has been fermented;
(c) adding an organic acid to the fermentation mixture after the fermenting, to terminate the fermenting and reduce the pH of the sugar ferment to between 2.3 and 3.7; and
(d) lysing microbial cells.

13. The method according to claim 12, wherein the microbe is a *Saccharomyces* species.

14. The method according to claim 12, wherein the fermentation mixture further includes one or more of monopotassium phosphate, magnesium sulphate, and urea.

15. The method according to claim 12, wherein the high metabolic stress in (b) is provided by a combination of high ionic strength and high osmotic pressure and oxidative stress.

16. The method according to claim 12, wherein (c) comprises adding between 4% and 10% (w/v) organic acid to the sugar ferment.

17. The method according to claim 12, wherein the organic acid is citric acid.

18. The method according to claim 12, wherein in (d) the lysing is accomplished by one or more of the following: adding urea; adding ammonium sulphate; exerting mechanical force; applying sonic stress; applying microwaves; applying heat; and applying high pressure.

19. A soil additive composition produced according to the method of claim 12.

20. The soil additive according to claim 1, wherein the conditions of high metabolic stress are provided by a combination of high ionic strength and high osmotic pressure and oxidative stress.

21. The soil additive according to claim 20, wherein the high ionic strength and high osmotic pressure are produced by reducing the amount of water in the fermentation mixture to between 0.5 x and 4.0 x (v/v) the volume of solids in the fermentation mixture.

22. The soil additive according to claim 20, wherein the oxidative stress is produced by reducing the oxygen level to between about 0.1 and 8.5 ppm dissolved $O_2$.

* * * * *

UNITED STATES PATENT AND TRADEMARK OFFICE
CERTIFICATE OF CORRECTION

PATENT NO. : 9,663,411 B2
APPLICATION NO. : 14/648013
DATED : May 30, 2017
INVENTOR(S) : Peter James Keating It is certified that error appears in the above-identified patent and that said Letters Patent is hereby corrected as shown below:

In the Claims

In Claim 10, "sigmasterol and sistosterol" should read -- stigmasterol and sitosterol --.

In Claim 11, "process" should read -- method --.

In Claim 12 part (b), at Column 50, Line 3, "in is" should read -- is --.

Signed and Sealed this
First Day of May, 2018

Andrei Iancu
*Director of the United States Patent and Trademark Office*